(12) United States Patent
Lin et al.

(10) Patent No.: US 8,921,113 B2
(45) Date of Patent: Dec. 30, 2014

(54) BUFFER KIT AND METHOD OF GENERATING A LINEAR PH GRADIENT

(71) Applicants: Shanhua Lin, Palo Alto, CA (US); Christopher A. Pohl, Union City, CA (US)

(72) Inventors: Shanhua Lin, Palo Alto, CA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 15 days.

(21) Appl. No.: 13/724,873

(22) Filed: Dec. 21, 2012

(65) Prior Publication Data

US 2014/0179008 A1    Jun. 26, 2014

(51) Int. Cl.
*G01N 30/34* (2006.01)
*G01N 30/02* (2006.01)
*G01N 33/68* (2006.01)
*B01D 15/16* (2006.01)
*C09K 15/30* (2006.01)
*B01D 15/36* (2006.01)

(52) U.S. Cl.
CPC .............. *C09K 15/30* (2013.01); *B01D 15/362* (2013.01); *B01D 15/168* (2013.01); *G01N 30/34* (2013.01)
USPC ................. 436/18; 436/8; 436/111; 436/119; 436/161; 436/163; 436/541; 436/86; 422/430; 422/70; 435/7.1

(58) Field of Classification Search
USPC ............... 436/8, 18, 106, 111, 119, 161, 163, 436/177, 178, 541, 86; 435/7.1; 422/430, 422/70; 210/656, 660, 662, 663, 198.2
See application file for complete search history.

(56) References Cited

U.S. PATENT DOCUMENTS

| | | |
|---|---|---|
| 4,801,687 A | 1/1989 | Ngo |
| 5,438,128 A | 8/1995 | Nieuwkerk |
| 5,447,612 A | 9/1995 | Bier et al. |
| 6,544,484 B1 | 4/2003 | Kaufman et al. |
| 6,568,245 B2 | 5/2003 | Kaufman et al. |
| 7,425,263 B2 | 9/2008 | Tsonev et al. |
| 7,662,930 B2 * | 2/2010 | Zhou ................... 530/390.1 |
| 7,790,025 B2 | 9/2010 | Tsonev et al. |
| 7,847,936 B2 | 12/2010 | Jarrell |
| 7,911,609 B2 | 3/2011 | Jarrell |
| 8,089,627 B2 | 1/2012 | Jarrell |
| 8,183,046 B2 | 5/2012 | Lu et al. |
| 8,366,899 B2 | 2/2013 | Albrecht et al. |
| 2004/0023405 A1 | 2/2004 | Bevan et al. |
| 2009/0218238 A1 | 9/2009 | Dasgupta et al. |
| 2012/0149875 A1 | 6/2012 | Johansson et al. |
| 2012/0184715 A1* | 7/2012 | Felgenhauer et al. ........ 530/383 |
| 2012/0239360 A1 | 9/2012 | Bello |
| 2012/0322976 A1 | 12/2012 | Wu et al. |
| 2013/0109102 A1 | 5/2013 | Li et al. |

FOREIGN PATENT DOCUMENTS

| | | |
|---|---|---|
| EP | 1273592 A2 | 1/2003 |
| WO | 8503578 | 8/1985 |
| WO | 2010068272 A1 | 6/2010 |
| WO | 2011028753 A1 | 3/2011 |
| WO | 2011091982 A1 | 8/2011 |
| WO | 2012054104 A1 | 4/2012 |
| WO | 2012082933 A1 | 6/2012 |
| WO | 2013006138 A1 | 1/2013 |
| WO | 2013028922 A1 | 2/2013 |
| WO | 2013028924 A1 | 2/2013 |
| WO | 2013066707 A1 | 5/2013 |

OTHER PUBLICATIONS

Bates et al., "Quasi-linear pH gradients for chromatofocusing using simple buffer mixtures: local equilibrium theory and experimental verification," J. of Chromatography A, 1998, 814, 43-54.
Bates et al., "High-performance chromatofocusing using linear and concave pH gradients formed with simple buffer mixtures: I. Effect of buffer composition on the gradient shape," J. of Chromatography A, 2000, 890, 25-36.
Farnan et al., "Multiproduct high-resolution monoclonal antibody charge variant separations by pH gradient ion-exchange chromatography," Anal. Chem., 2009, 81, 8846-8857.
Kang et al., "High-performance chromatofocusing using linear and concave pH gradients formed with simple buffer mixtures: II. Separation of proteins," J. of Chromatography A, 2000, 890, 37-43.
Rea et al "Valdaton of a pH gadient based ion-exchange chromatography method for high-resolution monoclonal antibody charge variant separations," J. of Pharm. and Biomed. Anal., 2011, 54, 317-323.
Tsonev et al., "Improved resolution in the separation of monoclonal antibody isoforms using controlled pH gradients in IEX chromatography," Amer. Biotech. Lab., Jan. 2009, 3 pages.
plSep anion, cation and combined ion exchange chromatography for separation of proteins and charged molecules by external pH gradients, CryoBioPhysica, 4 pages.
Ahamed et al., "pH-gradient ion-exchange chromatography: an analytical tool for design and optimization of protein separations," J. of Chromatography A, 1164, 2007, 181-188.

(Continued)

*Primary Examiner* — Maureen Wallenhorst
(74) *Attorney, Agent, or Firm* — Timothy J. Ohara

(57) ABSTRACT

A buffer kit includes a first eluent and second eluent. The first eluent solution includes at least four buffer salts where at least three of the four buffer salts are a monovalent buffer salt, have a net negative charge or a net neutral zwitterionic charge, and include a sulfonate group and an amine. The second eluent solution includes at least four buffer salts where at least three of the four buffer salts are a monovalent buffer salt, have a net negative charge or a net neutral zwitterionic charge, and include a sulfonate group and an amine. The first eluent solution has a first pH and the second eluent solution has a second pH where the first pH and second pH are different values. The buffer kit provides a linear pH gradient that forms an approximately straight line from at least the first pH to the second pH.

41 Claims, 11 Drawing Sheets

(56) References Cited

OTHER PUBLICATIONS

Kroener et al., "Systematic generation of buffer systems for pH gradient ion exchange chromatography and their application," J. of Chromatography A, 2013, doi:10.1016/j.chroma.2013.02.017.

Zhang et al., "Improving pH gradient cation-exchange chromatography of monoclonal antibodies by controlling ionic strength," J. of Chromatography A, 1272, 2013, 56-64.

Lin et al., "A Novel pH Gradient Separation Platform for Monoclonal Antibody (MAb) Charge-Variant Analysis," www.thermoscientific.com/dionex, 7 pgs., 2013.

Rea et al., "Monoclonal Antibody Development and Physicochemical Characterization by High Performance Ion Exchange Chromatography," Innovations in Biotech, Dr. Eddy C. Agbo (Ed.), 439-464, 2012.

Rea et al., "Validation of a pH gradient-based ion-exchange chromatography method for high-resolution monoclonal antibody charge variant separations," J Pharm Biomed Anal., 54(2), 317-23, 2011 (Epub Sep. 29, 2010).

Zhang et al., "Improving pH gradient cation-exchange chromatography of monoclonal antibodies by controlling ionic strength," J Chromatogr A, 1272, 56-64, 2013 (Epub Nov. 29, 2012).

\* cited by examiner

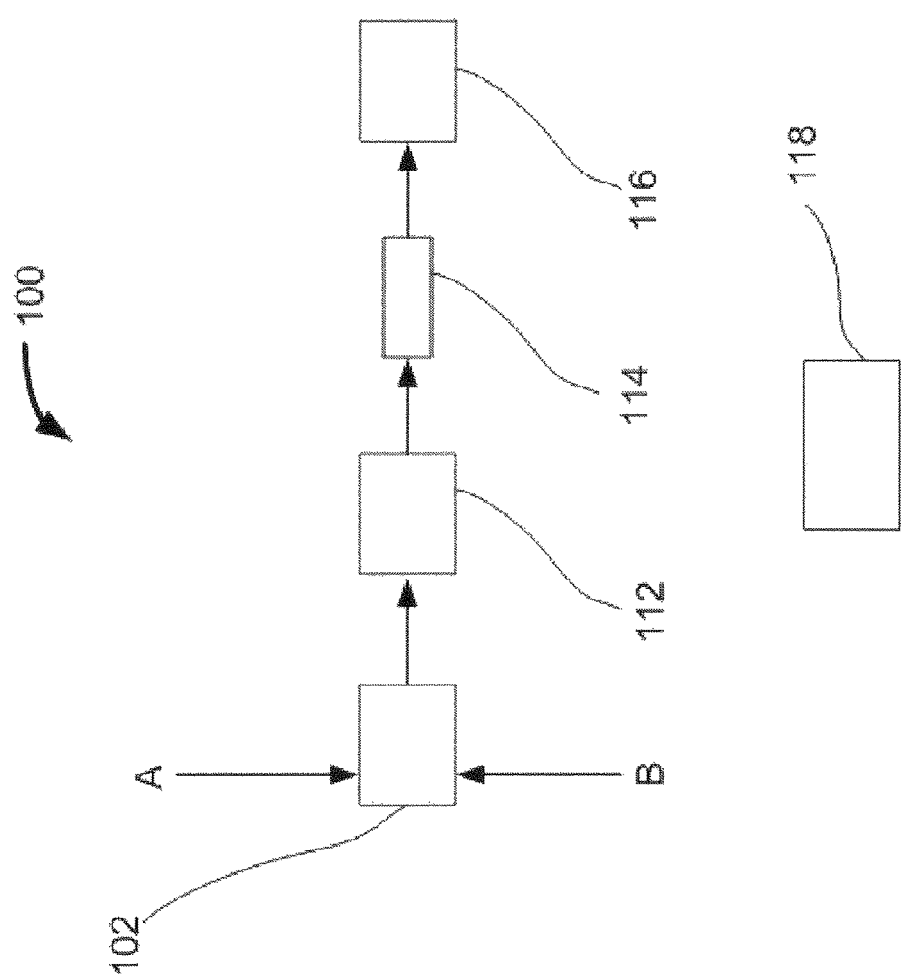

BUFFER KIT AND METHOD OF GENERATING A LINEAR PH GRADIENT

BACKGROUND

Ion exchange chromatography (IEC) is a widely used analytical technique for the chemical analysis and separation of charged molecules. IEC involves the separation of one or more analyte species from other matrix component present in a sample. The analytes are typically ionic so that they can have an ionic interaction with a stationary phase. In IEC, the stationary phase is derivatized with ionic moieties that ideally will bind to the analytes and matrix components with varying levels of affinity. An eluent is percolated through the stationary phase and competes with the analyte and matrix components for binding to the ionic moieties. The eluent is a term used to describe a liquid solution or buffer solution that is pumped into a chromatography column inlet. During this competition, the analyte and matrix components will elute off of the stationary phase as a function of time and then be subsequently detected at a detector. Examples of some typical detectors are a conductivity detector, a UV-VIS spectrophotometer, and a mass spectrometer. Over the years, IEC has developed into a powerful analytical tool that is useful for creating a healthier, cleaner, and safer environment where complex sample mixtures can be separated and analyzed for various industries such as water quality, environmental monitoring, food analysis, pharmaceutical, and biotechnology.

In the biotechnology industry, there have been numerous breakthrough discoveries in developing therapeutic drugs that are based on proteins. Monoclonal antibodies (MAbs) represent a particular type of protein therapeutic that has been successful in treating diseases such as Crohn's disease, rheumatoid arthritis, non-Hodgkin lymphoma, and metastatic breast cancer. Given the past successes in MAb technology, there is a continuing interest in developing new therapeutic applications of MAb technology, and more particularly, in accelerating the discovery, development, and screening process, which has heretofore been expensive and time consuming.

Recombinant MAbs are highly heterogeneous due to modifications such as C-terminal lysine truncation, N-terminal pyroglutamate formation, deamidation, sialylation, glycation, and glycosylation. Some of these modifications can cause a variation in the charge of a MAb. For example, deamidation and sialylation will introduce negatively charged acidic moieties on the MAb. An array of positively charged MAb variants can be created through a C-terminal lysine truncation. Traditionally, an eluent salt gradient with cation ion-exchange chromatography has been used to characterize MAb charge variants. However, method development is often required to configure the salt gradient and separation parameters every time a new MAb candidate requires characterization. For example, such parameters may include buffer salt type, buffer salt concentration, non-buffer salt type, non-buffer salt concentration, flow rates, time profile for establishing the change in proportions of the eluent solution components, and rate of pH change per unit time. Applicants believe that there is a need to develop a buffer kit and system that can provide a linear pH gradient over a wide pH range and can be used to characterize a wide variety of proteins (e.g., MAbs) with little to no modification of the separation parameters for each new candidate.

SUMMARY

A buffer kit including a first eluent solution and a second eluent solution. The first eluent solution includes at least four buffer salts where at least three of the four buffer salts are a monovalent buffer salt, have a net negative charge or a net neutral zwitterionic charge over a pH range of 6 to 10, and include a sulfonate group and an amine, where the first eluent solution has a first pH of 6 and a total buffer salt concentration of greater than 25 millimolar. The second eluent solution includes at least four buffer salts where at least three of the four buffer salts are a monovalent buffer salt, have a net negative charge or a net neutral zwitterionic charge over a pH range of 6 to 10, and include a sulfonate group and an amine, where the second eluent solution has a second pH of 10 and a total buffer salt concentration of greater than 25 millimolar. The buffer kit provides a linear pH gradient, based on a function of time and pH values, that forms an approximately straight line for at least a pH range of pH 6 to pH 10.

In regards to the above buffer kit, the first eluent solution and the second eluent solution may each further include a monovalent non-buffer ionic salt. The monovalent non-buffer ionic salt may be sodium chloride, sodium methanesulfonate, potassium chloride, or a combination thereof and have a concentration of 15 millimolar or greater.

In regards to the above buffer kit for the first eluent solution, a highest buffer concentration of the at least four buffer salts is not greater by more than 60% of a lowest buffer concentration of the at least four buffer salts. Similarly, for the second eluent solution, a highest buffer concentration of the at least four buffer salts is not greater by more than 60% of a lowest buffer concentration of the at least four buffer salts.

In regards to the above buffer kit, the four buffer salts of either the first eluent solution or the second eluent solution may include a first buffer salt, a second buffer salt, a third buffer salt, and a fourth buffer salt. The first, second, third, and fourth buffer salts may respectively be 2-(N-morpholino)ethanesulfonate (MES), 3-(N-morpholino)propanesulfonate (MOPS), N-[tris(hydroxymethyl)methyl]-3-aminopropanesulfonate (TAPS), and 3-(cyclohexylamino)-2-hydroxy-1-propanesulfonate (CAPSO). Alternatively, the first, second, third, and fourth buffer salts may respectively be 2-(N-morpholino)ethanesulfonate (MES), 2-[bis(2-hydroxyethyl)amino]ethanesulfonate (BES), (tris(hydroxymethyl)methylamino)propane-1-sulfonate (TAPS), and 3-(cyclohexylamino)-2-hydroxy-1-propanesulfonate (CAPSO).

In regards to the above buffer kit, the at least four buffer salts each have a net negative charge or a net neutral charge over a pH range of 6 to 10.

In regards to the above buffer kit, one of the at least four buffer salts is selected from the group consisting of TRIS and phosphate In regards to the above buffer kit, the at least four buffer salts of the first eluent solution and second eluent solution, each include a first buffer salt that has a first pKa, a second buffer salt that has a second pKa, a third buffer salt that has a third pKa, and a fourth buffer salt that has a fourth pKa. The first pKa is the smallest of the four pKa values and the fourth pKa is the largest of the four pKa values where the first pKa is the same as the first pH value and that the fourth pKa is the same as the second pH value. The first difference between the second pKa and the first pKa is less than 1.5. The second difference between the third pKa and the second pKa is less than 1.5. The third difference between the third pKa and the fourth pKa that is less than 1.5.

In regards to the above buffer kit, the straight line for the pH range of pH 6 to pH 10 has a correlation coefficient greater than 0.97. Using a different metric, the straight line for the pH range of pH 6 to pH 10 can have a mean absolute percent error of less than 1.4%.

In regards to the above buffer kit, the amine can be in a protonated ammonium form.

A method of separating at least one analyte from matrix components in a sample with a chromatographic separation device using a gradient eluent flow having a linear pH gradient from a first pH value to a second pH value as a function of time is described. The method includes injecting the sample into an injection valve where the injection valve is in fluidic communication with the chromatographic separation device. A first eluent solution that has the first pH value can be pumped into the chromatographic separation device. The first eluent solution includes a first buffer salt, a second buffer salt, a third buffer salt, and a fourth buffer salt. A second eluent solution that has the second pH value can be pumped into the chromatographic separation device. The second eluent solution includes a first buffer salt, a second buffer salt, a third buffer salt, and a fourth buffer salt. For both the first and second eluent solutions, the first buffer salt has a first pKa, the second buffer salt has a second pKa, the third buffer salt has a third pKa, and the fourth buffer salt has a fourth pKa. The first pKa is the smallest of the four pKa values and the fourth pKa is the largest of the four pKa values. The first pKa is the same as the first pH value and the fourth pKa is the same as the second pH value. The buffer salts can be selected so that the pKa values approximately and uniformly span between the first pH and second pH values. A first difference between the second pKa and the first pKa is less than 1.5, a second difference between the third pKa and the second pKa is less than 1.5, and a third difference between the third pKa and the fourth pKa is less than 1.5. A proportion of the pumped first eluent solution and the pumped second eluent solution can be varied as a function of time. A linear pH gradient can be generated, based on a function of time and pH values, that forms an approximately straight line from the first pH value to the second pH value. The sample can be eluted through the chromatographic separation device. The analyte can be separated from matrix components in the sample. The analyte can then be detected at a detector.

In regards to the above method, the linear pH gradient is an approximately straight line with a correlation coefficient greater than 0.97, where the first pH value is 6 and the second pH value is 10. Using a different metric, the linear pH gradient is an approximately straight line with a mean absolute percent error of less than 1.4%, where the first pH value is 6 and the second pH value is 10.

In regards to the above method, a linear conductivity gradient is generated, at the same time, as the step of generating the linear pH gradient. The generated linear pH gradient has increasing pH values as a function of time and the generated linear conductivity gradient has increasing conductivity values as a function of time.

In regards to the above method, the chromatographic separation device includes a cation exchange resin where each of the buffer salts for the first and second eluent solutions do not bind to the cation exchange resin.

In regards to the above method, the analyte includes an antibody.

In regards to the above method, the generated linear pH gradient is formed in the chromatographic separation device.

In regards to the above method, the first buffer salt includes 2-(N-morpholino)ethanesulfonate. The second buffer salt can be selected from 2-[bis(2-hydroxyethyl)amino]ethanesulfonate, MOPS, or phosphate. The third buffer salt can be selected from N-[tris(hydroxymethyl)methyl]-3-aminopropanesulfonate or TRIS. The fourth buffer salt can be 3-(cyclohexylamino)-2-hydroxy-1-propanesulfonate.

In regards to the above method, the first eluent solution and second eluent solution further includes a monovalent non-buffer ionic salt. The monovalent non-buffer ionic salt can selected sodium chloride, potassium chloride, sodium methanesulfonate, or a combination thereof.

In regards to the above method, the first pH value is 6 and the second pH value is 10. The first and second eluent solutions can each have a total buffer salt concentration of greater than 25 millimolar. The monovalent non-buffer ionic salt can have a concentration of 15 millimolar or greater.

In regards to the above method, for the first eluent solution, a highest buffer concentration of the four buffer salts is not greater by more than 60% of a lowest buffer concentration of the four buffer salts. Similarly, for the second eluent solution, a highest buffer concentration of the four buffer salts is not greater by more than 60% of a lowest buffer concentration of the four buffer salts.

In regards to the above method, before the pumping of the first eluent solution and the second eluent solution into the chromatographic separation device, first eluent solution and the second eluent solution can be mixed together.

In regards to the above method, two or more solutions sources can be inputted into a pump. A combination of the two or more solutions sources together includes the first buffer salt, the second buffer salt, the third buffer salt, and the fourth buffer salt of the first eluent solution. Next, the first eluent solution can be formed from the two or more solution sources. Similarly, the second eluent solution can be formed from two or more solution sources.

In regards to the above method, each of the buffer salts are a monovalent buffer salt, have a net negative charge or a net neutral zwitterionic charge over a pH range ranging from the first pH value to the second pH value, and include a sulfonate group and an amine.

In regards to the above method, the amine can be in a protonated ammonium form.

In a second embodiment of a buffer kit, it includes a first eluent solution and a second eluent solution. The first eluent solution consists of a first buffer salt, a second buffer salt, a third buffer salt, a fourth buffer salt, and a monovalent non-buffer ionic salt. The first eluent solution has a first pH of 6 and a total buffer salt concentration of greater than 25 millimolar. The second eluent solution consists of a first buffer salt, a second buffer salt, a third buffer salt, a fourth buffer salt, and a monovalent non-buffer ionic salt. The second eluent solution has a second pH of 10 and a total buffer salt concentration of greater than 25 millimolar. Each of the buffer salts are a monovalent buffer salt, have a net negative charge or a net neutral zwitterionic charge, and include a sulfonate group and an amine.

In regards to the second embodiment of the buffer kit, the four buffer salts of the first eluent solution and second eluent solution, each include a first buffer salt that has a first pKa, a second buffer salt that has a second pKa, a third buffer salt that has a third pKa, and a fourth buffer salt that has a fourth pKa. The first pKa is the smallest of the four pKa values and the fourth pKa is the largest of the four pKa values. The first pKa is the same as the first pH value and that the fourth pKa is the same as the second pH value. The at least four buffer salts have a first difference between the second pKa and the first pKa that is less than 1.5, a second difference between the third pKa and the second pKa that is less than 1.5, and a third difference between the third pKa and the fourth pKa that is less than 1.5.

In regards to the second embodiment of the buffer kit, for the first eluent solution, a highest buffer concentration of the four buffer salts is not greater by more than 60% of a lowest buffer concentration of the four buffer salts. Similarly, for the second eluent solution, a highest buffer concentration of the four buffer salts is not greater by more than 60% of a lowest buffer concentration of the four buffer salts.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

FIG. 11 is an exemplary ion chromatography system suitable for use with the buffer kits described herein.

DETAILED DESCRIPTION OF EMBODIMENTS

Figure 1:
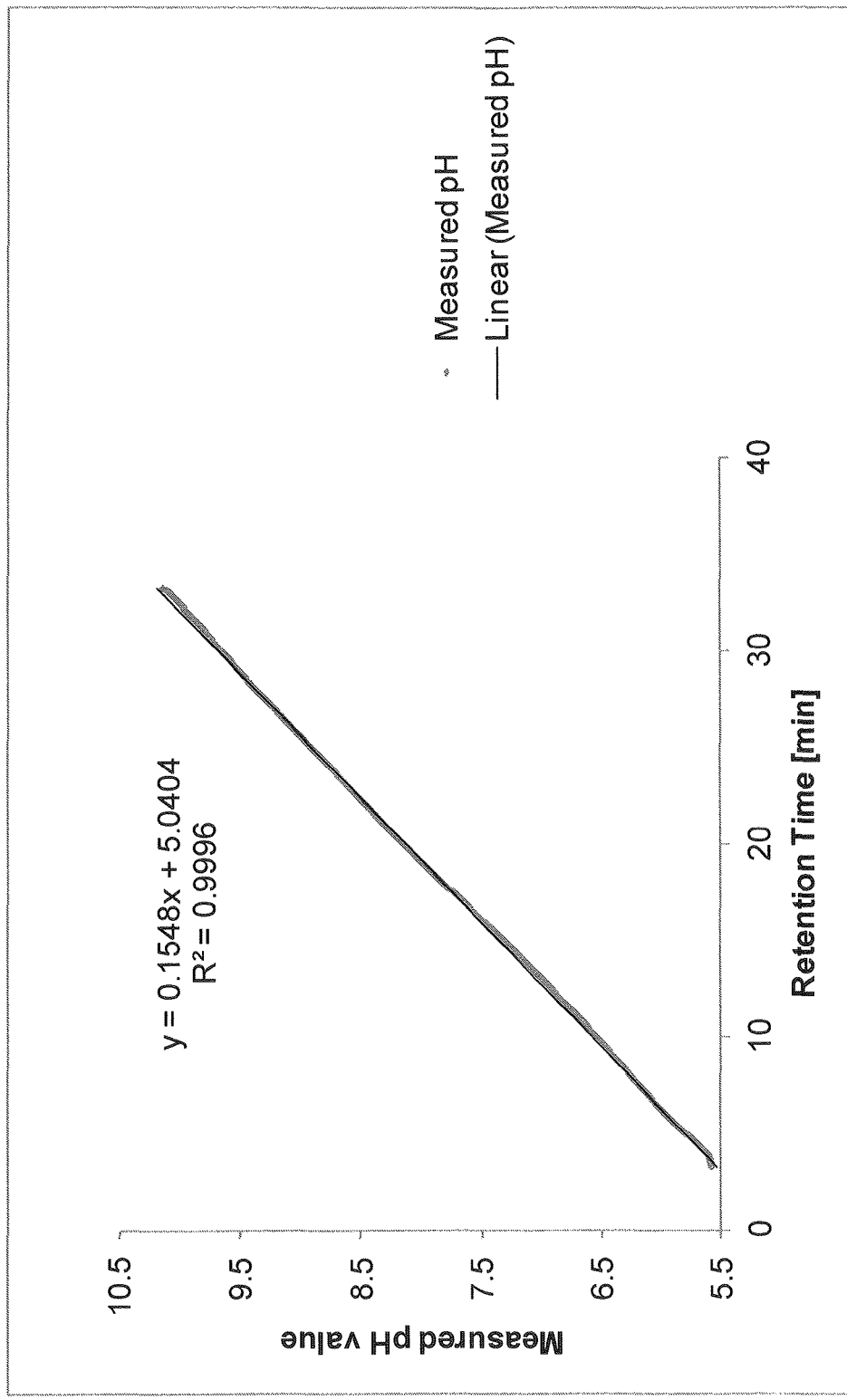
FIG. 1 is a graph showing measured pH values as a function of time using a buffer kit that includes the buffer salts of MES, BES, TAPS, and CAPSO.

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

The net charge of MAb molecules can be used as a basis for characterizing and separating a MAb candidate. During development, a MAb sample will typically contain a variety of MAb variants with slightly different chemical structures. These MAb variants are typically referred to as charge variants because of the varying levels of net charge that can be ascribed to acid/base groups. In a typical sample, many of the MAb variants will have an individually distinct pI value. The pI value represents the pH value at which the particular MAb variant will have a net neutral charge. The pI value may also be referred to as an isoelectric point. An array of pI values associated with a particular MAb sample can provide a fingerprint that is useful in characterizing the sample. For example such fingerprint profiles can be used in processes like identification, purity, batch reproducibility, and researching the efficacy of particular charge variants. It should be noted that the buffer kit described herein should not be limited to only to the analysis of MAb samples and that they can be used for the analysis of a wide variety of proteins and other molecules that have acid/base moieties.

Over a range of pH values from pH 6 to 10, MAbs will typically have a net positive charge for at least a portion of this range. For this reason, cation exchange chromatography is well-suited for separating and characterizing MAb samples. In an embodiment, a MAb sample can be injected onto a cation exchange column where the eluent is initially at a relatively low pH. This ensures that most of the MAb variants are positively charged, and thus, will bind to the cation exchange stationary phase. A linear pH gradient can be applied to the column causing the pH to increase linearly as a function of time. The increasing pH will titrate the acid groups on the MAb and cause the net positive charge to decrease. For example, protonated amine groups will transition from a positive charge to neutral and carboxylic acid groups will transition from neutral to a negative charge. At a certain pH during the linear pH gradient, the net charge will eventually become neutral (i.e. isoelectric point). The affinity of the MAb variant to the cation exchange column will decrease significantly when the MAb variant has a net neutral charge, and thus, will result in it being eluted from the column.

The following will describe a buffer kit that provides a linear pH gradient. The linear pH gradient represents changing pH values based on a function of time where the pH values over a range of time form an approximately straight line for at least a pH range of about pH 6 to about pH 10. Applicant believes that a linear pH gradient with ion exchange chromatography will provide a platform method for characterizing a MAb sample where minimal to no changes in the characterization process will be needed. Applicant also believes that the degree of straightness of the linear pH gradient is critical for characterizing the MAb samples and also for expanding the resolution of the separation when using a narrower pH range with a decreased rate of pH change per unit time.

In an embodiment, the buffer kit can include a first eluent solution and a second eluent solution. Note that an eluent solution can be a solution that is used to elute a sample from an ion exchange stationary phase. The eluent solutions may be packaged into a respective liquid container or vial. To reduce the shipping weight, the eluent solutions may be packaged at a 10× concentration where the users can dilute at the testing site to the appropriate concentration range such as about a 1× range. It should be noted that the buffer kit described herein should not be limited to only two eluent solutions and that buffer kits can be implemented using more than two eluent solutions.

Regarding the first eluent solution, it may include at least four buffer salts where at least three of the four buffer salts have particular properties, which are a) the buffer salts are monovalent buffer salts, b) have a net negative charge or a net neutral zwitterionic charge over a pH range of about 6 to about 10, and c) include a sulfonate group and an amine. The following will describe the particular properties a) to c) in more detail.

A monovalent buffer salt is a buffer that has only one acid/base moiety. For the buffer kits described herein, the acid/base moiety should have a pKa value in between the relevant pH range, which in this case is from about pH 6 to 10. In addition, the monovalent buffer salt can have only one of three charge states, which are a single positive charge, no net charge (i.e., neutral or zwitterionic charge), or a single negative charge. Applicant believes that where the at least three of four buffer salts are polyvalent, the buffer kit will provide varying buffer capacity at different pH values, and in turn, result in less linear pH gradients and a more difficult to implement separation method.

The at least three buffer salts should each include either a net negative charge or net neutral zwitterionic charge over the pH range of about 6 to about 10 so that the buffer salts will not strongly associate with or bind to the cation exchange column. Cation exchange material usually has a negative charge for binding to positively charged cations. Thus, a net negatively charged buffer salt should not bind to the negatively charged cation exchange moieties because of ionic repulsion. A net neutral zwitterionic charged buffer salt should not bind to the negatively charged cation exchange material because of a lack of net ionic attraction between a neutral and negatively charged species. In contrast, a positively charged buffer salt should bind to the negatively charged cation exchange material because of ionic attraction. The ionic bonding of a positively charged buffer salt to the cation exchange material may affect the buffering capability of the buffer salt and interfere with the linearity of the pH gradient. In an embodiment, the buffer salts are not retained by nor completely excluded from the stationary phase in a manner that allows the buffer salts to effectively buffer both the mobile phase and the stationary phase. Note that if a buffer salt species is excluded from the stationary phase, then it cannot buffer the stationary phase and facilitate the elution of the analyte in a manner similar to other buffer salts that are not excluded from the stationary phase. Additionally, a buffer salt that is retained by the stationary phase can cause a deviation between the mobile phase pH and the stationary phase pH which is dependent upon the retention characteristics of the buffer on the stationary phase.

The at least three buffer salts should each further include a sulfonate group and an amine. In an embodiment, the amine group may be a primary, secondary, or tertiary amine. The buffer salt may be in the form where the hydrogen from the sulfonic acid group protonates the amine group to form a positively charged moiety and a negatively charged sulfonate group, which together form a zwitterion. The buffer salt may also be in the form where the protonated amine group has a negative counterion such as chloride and the sulfonate group has positive counterion such as sodium. It should be noted that many buffer salts that include a sulfonate group and an amine group may be referred to as a "Good's buffer."

Although not expressly described in the name of a particular buffer salt, a person having ordinary skill in the art will understand that the designation of the term "sulfonate" as part of the name of the buffer salt should not limit the buffer salt to only the negatively charged sulfonate state and that it can also be in the sulfonic acid form under low pH conditions. Further, a person having ordinary skill in the art will understand that the designation of the term "amine" as part of the name of a buffer salt should not limit the buffer salt to only the neutral charge free amine state and that it can also be in the protonated ammonium form with a counteranion when the buffer is slightly acidic.

In an embodiment, the first eluent solution may have a first pH of about 6 and total buffer salt concentration of greater than about 25 millimolar. The first pH of 6 was selected when separating MAb charged variants because a significant portion of the MAb variants in the sample have a net positive charge that causes binding to the cation exchange column. The buffer salt concentration of the first eluent solution can be selected so that the buffering capacity is greater than both the MAb sample and the cation exchange material.

The buffer kit includes a second eluent solution that can be mixed with the first eluent solution to create a linearly increasing pH gradient. The second eluent solution can have a second pH that is greater than the first pH of the first eluent solution. Similar to the first eluent solution, the second eluent solution may include at least four buffer salts where at least three of the four buffer salts have particular properties, which are a) the buffer salts are monovalent buffer salts, b) have a net negative charge or a net neutral zwitterionic charge over a pH range of about 6 to about 10, and c) include a sulfonate group and an amine.

The second eluent solution may have a second pH of about 10 and total buffer salt concentration of greater than about 25 millimolar. The second pH of 10 was selected when separating MAb charged variants because most MAb variants will not have a pI greater than 10. Thus, during a linear gradient from pH 6 to pH 10, essentially all of the MAb charged variants will have transitioned to a net neutral value causing them to elute off of the cation exchange column. Similar to the first eluent, the buffer salt concentration of the second eluent solution can be selected so that the buffering capacity is greater than both the MAb sample and the cation exchange material.

In an embodiment, the at least four buffer salts may be the same chemical species for both the first eluent solution and the second eluent solution. For example, the first eluent solution and the second eluent solution both contain the following four buffer salts, which are 2-(N-morpholino)ethanesulfonate (MES), 2-[bis(2-hydroxyethyl)amino]ethanesulfonate (BES), N-[tris(hydroxymethyl)methyl]-3-aminopropanesulfonate (TAPS), 3-(cyclohexylamino)-2-hydroxy-1-propanesulfonate (CAPSO).

The at least four buffer salts of the first eluent solution and second eluent solution may each include a first buffer salt that has a first pKa, a second buffer salt that has a second pKa, a third buffer salt that has a third pKa, and a fourth buffer salt that has a fourth pKa. The first pKa may be the smallest of the four pKa values and the fourth pKa may be the largest of the four pKa values. The buffer salts can be selected so that the first pKa is about the same as the first pH value and that the fourth pKa is about the same as the second pH value. More particularly, the buffer salts can be selected so that the first pKa is within 0.5 pH units of the first pH value and that the fourth pKa is within 0.5 pH units of the second pH value.

The buffer salts can also be selected so that the pKa values approximately and uniformly span between the first pH and second pH values. In an embodiment, there is a first difference between the second pKa and the first pKa that is less than about 1.5, a second difference between the third pKa and the second pKa that is less than about 1.5, and a third difference between the third pKa and the fourth pKa that is less than about 1.5. The differences of the four pKa values can be selected to range from about 0.5 to about 1.5 pH units so that there is a relatively uniform buffering capacity from the first pH to the second pH. Applicant believes that by selecting buffer salts with pKa's that provide an approximately equal first, second, third difference value will result in buffer kits that provide linear pH gradients. In an embodiment, the first, second, third, and fourth pKa values may be about 6.1, 7.1, 8.4, and 9.6 at 25° C. It should be noted that all pKa values stated herein are stated with respect to 25° C. unless explicitly stated to be at a different temperature.

In an alternative embodiment, one or more of the buffer salts of the first eluent solution may be a different chemical species than the buffer salts of the second eluent solution. For example, the first eluent solution may include MES, BES, TAPS, and CAPSO and the second eluent solution may include MES, MOPS, TAPS, and CAPSO. Even though the second buffer salt of the second eluent solution is a different chemical species, this buffer kit will still provide a linear pH gradient.

In an embodiment, the buffer salt concentration values of the first eluent solution and second eluent solution may be selected to have boundary conditions. For instance, the eluent solutions can each have a lowest and a highest buffer concentration of the at least four buffer salts. The buffer salt concentration values can be selected so that the highest buffer concentration is not greater by more than about 60% of the lowest buffer concentration.

An example of selected buffer salt concentration values for the first eluent solution can include 16 mM MES, 10 mM BES, 12 mM TAPS, and 10 mM CAPSO. Here, the lowest buffer salt concentration is 10 mM for the BES and 10 mM for the CAPSO, and the highest buffer salt concentration is 16 mM for the MES. Thus, the 16 mM MES is not greater by more than 60% of the 10 mM BES or CAPSO.

An example of selected buffer salt concentration values for the second eluent solution can include 10 mM MES, 12 mM BES, 14 mM TAPS, and 16 mM CAPSO. Here, the lowest buffer salt concentration is 10 mM for the MES, and the highest buffer salt concentration is 16 mM for the CAPSO. Thus, the 16 mM CAPSO is not greater by more than 60% of the 10 mM MES.

It should be noted that Applicant empirically determined the set of buffer concentration that provided a linear pH gradient and that the buffer kit embodiments described herein should not be limited to these particular set of buffer concentrations. Alternatively, it is also possible to use weak acid and weak base dissociation constants, and standard analytical equations to calculate a set of buffer concentrations that provide a linear pH gradient. However, such analysis is computationally intensive, and thus, a software program can be suitable for modeling the pH profile or a particular set of buffer concentrations, such as, for example, the software program described in U.S. Pre-Grant Publication No. 2012/0239360, which is hereby incorporated by reference herein.

In an embodiment, the first eluent solution and the second eluent solution may each further include a monovalent non-buffer ionic salt such as for example, sodium chloride, potassium chloride, or sodium methanesulfonate. The monovalent non-buffer ionic salt includes only anions and cations having a single charge that is positive or negative. In addition, the monovalent non-buffer ionic salt does not have a weak acid or weak base functionality for providing any appreciable buffering capacity. For example, the first eluent solution and the second eluent solution may each include a sodium chloride concentration of about 15 millimolar or greater. Applicant believes that the presence of the monovalent non-buffer ionic salt facilitates the separation on ion exchange columns and also allows for lower concentrations of the buffer salts to be used. As a result, the buffer concentrations in the buffer kits can be reduced, which provides a lower cost system in regards to reagent costs and, at the same time, provides linear pH gradients suitable for separating protein samples. In addition, Applicant has found that the use of monovalent non-buffer ionic salt tends to increase the operational lifetime of the separation column providing further cost savings.

The first and second eluent solutions can each include at least four buffer salts where at least three of four buffer salts are selected from a first buffer salt, a second buffer salt, a third buffer salt, and a fourth buffer salt. The first buffer salt may include 2-(N-morpholino)ethanesulfonate (MES). The second buffer salt may include N,N-bis(2-hydroxyethyl)-2-aminoethanesulfonate (BES) or 3-(N-morpholino)propanesulfonate (MOPS). The third buffer salt may include N-[tris(hydroxymethyl)methyl]-3-aminopropanesulfonate (TAPS) or N-(2-hydroxyethyl)piperazine-N-(4-butanesulfonate) (HEPBS). The fourth buffer salt may include 3-(cyclohexylamino)-2-hydroxy-1-propanesulfonate (CAPSO) or 2-(cyclohexylamino)ethanesulfonate (CHES). It should be noted that any combination that uses at least three of the first, second, third, or fourth buffer salts described above can provide a buffer kit suitable for generating a linear pH gradient from about pH 6 to about pH 10. In addition, the above buffer salts can be modified where the sulfonate moieties can have various alkyl chain lengths such as, for example, ethyl sulfonate, propyl sulfonate, butyl sulfonate, and hydroxypropyl sulfonate. It should be noted that the above buffer salts are exemplary and that the buffer kits described herein for generating linear pH gradients should not be limited to the above exemplary buffer salts.

In an embodiment, for both the first eluent solution and the second eluent solution, the at least four buffer salts may be selected so that one or more of the buffer salts do not have all of the particular properties of a) to c) described above. For example, each buffer salt can have a net negative charge or a net neutral charge over a pH range of about 6 to about 10 (feature b), but not necessarily have features a) and c)). One or more of the buffer salts may include one or more of the following characteristics, which are being a polyvalent buffer, and not including both a sulfonate group and an amine. For example, one of the buffer salts may be phosphate. Phosphate is only negatively charged over a pH range of about 6 to about 10, is a polyvalent buffer, and does not have an amine group or a sulfonate group. Phosphate that is used with the buffer kits described herein may be in the form of monobasic, dibasic, and/or tribasic where the counterion is sodium and/or potassium. Other buffer salts that contain phosphate functions suitable for use in the buffer kits described herein are pyrophosphate and tripolyphosphate.

In another embodiment, for both the first eluent solution and the second eluent solution, one or more of the buffer salts may include one or more of the following characteristics, which are having a net positive charge or a net neutral charge over a pH range of about 6 to about 10 and not include sulfonate group. For example, one of the buffer salts may be tris(hydroxymethyl)aminomethane (TRIS). TRIS can be either neutral or positively charged over a pH range of about 6 to about 10 and does not have a sulfonate group. Surprisingly, Applicant found that the inclusion of a buffer salts that have one or more of the following characteristics such as being a polyvalent buffer salt, positively charged over a pH range of about 6 to 10, not having a sulfonate group, or not having an amine did not significantly interfere with the pH linearity of the buffer kit over the pH range so long as at least three buffer salts were included that each had the following properties, which are a) the buffer salts are monovalent buffer salts, b) have a net negative charge or a net neutral zwitterionic charge over a pH range of about 6 to about 10, and c) include a sulfonate group and an amine. Thus, the use of TRIS or phosphate as one of the buffer salts in the buffer kits described herein can still provide a sufficiently linear pH gradient.

The following will describe a slightly different buffer kit embodiment that those described above. This embodiment is different in that that it consists of four buffer salts and one monovalent non-buffer ionic salt and essentially does not have any other added buffer salts or monovalent non-buffer ionic salts. This buffer kit includes a first eluent solution and a second eluent solution. The first eluent solution consists of a first buffer salt, a second buffer salt, a third buffer salt, a fourth buffer salt, and sodium chloride, where the first eluent solution has a first pH of about 6 and a total buffer salt concentration of greater than about 25 millimolar. The second eluent solution consists of a first buffer salt, a second buffer salt, a third buffer salt, a fourth buffer salt, and sodium chloride, where the second eluent solution has a second pH of about 10 and a total buffer salt concentration of greater than about 25 millimolar. For both the first and second eluent solutions, each of the buffer salts are a monovalent buffer salt, have a net negative charge or a net neutral zwitterionic charge, and include a sulfonate group and an amine.

In another embodiment of a buffer kit, three buffer salts may be used instead of four where the linear pH range spans three pH units instead of four. For example, the first and second eluent solutions may each include BES, TAPS, and CAPSO where the linear pH gradient spans from about pH 7 to about pH 10.

In yet another embodiment of a buffer kit, at least five buffer salts may be used instead of four where the linear pH range spans five pH units instead of four. For example, the first and second eluent solutions may each include a fifth buffer salt where the linear pH gradient spans from about pH 6 to about pH 11. The fifth buffer salt may be 3-(cyclohexylamino)-1-propanesulfonate (CAPS) that has a pKa at 10.4, or 4-(cyclohexylamino)-1-butanesulfonate (CABS) that has a pKa at 10.7.

Now that the buffer kit has been described, the following will describe a chromatographic system for use with the buffer kit that generates a linear pH gradient. FIG. 11 illustrates an embodiment of a chromatography system 100 that is configured for a gradient buffer generation that includes two or more eluent solutions. Chromatography system 100 may include a pump 102, an injection valve 112, a chromatographic separation device 114, a detector 116, and a microprocessor 118.

Pump 102 can be configured to pump a liquid from a liquid source and be fluidically connected to injection valve 112. The liquid may be an eluent solution having a plurality of buffer salts. The liquid source can be in the form of a container that contains the liquid and can be fluidically attached to an input of pump 102. Pump 102 can be configured to transport the liquid at a pressure ranging from about 20 PSI to about 15,000 PSI. It should be noted that the pressures denoted herein are listed relative to an ambient pressure (13.7 PSI to 15.2 PSI). Pump 102 may be in the form of a high pressure liquid chromatography (HPLC) pump. In addition, pump 102 can also be configured so that the liquid only touches an inert portion of pump 102 to prevent a significant amount of impurities from leaching out. In this context, significant means an amount of impurities that would interfere with the intended measurement. For example, the inert portion can be made of polyetherether ketone (PEEK) or at least coated with a PEEK lining, which does not leach out a significant amount of ions when exposed to a liquid.

In addition, pump 102 can be configured to intake more than one type of eluent solution. As illustrated in FIG. 11, the letters A and B indicate that two different types of eluent solutions can be inputted into pump 102. Pump 102 can include a proportioning valve that controls a proportion of A (e.g., first eluent solution) and B (e.g., second eluent solution) that is outputted. In an embodiment, the proportion of A and B pumped can both be independently changed as a function of time.

It should be noted that more than two solution sources can be used to create the linear buffer gradient described herein. For example, pump 102 may be a quaternary pump with four intakes that are attached to four separate solution source containers A, B, C, and D. The first eluent solution can be created in situ within pump 102 by allocating the components (buffer salts and monovalent non-buffer ionic salts) of the eluent solution to two or more intake source containers. For example, container A can have 32 mM MES, 20 mM BES, and 30 mM NaCl at pH 5.6 and container B can have 24 mM TAPS, 20 mM CAPSO and 30 mM NaCl at pH 5.6. As such, pump 102 can mix both containers A and B in equal proportions so that the combination forms essentially the first eluent solution with a buffer salt concentration consistent with the prior embodiments. In a similar manner, the second eluent solution can also have the buffer salts and monovalent non-buffer ionic salts allocated into 2 or more containers.

The following will describe another embodiment of allocating portions of the first and second eluent solutions into four containers that are each inputted into an intake portion of the quaternary pump. This embodiment provides a platform so that the parameters can be adjusted quickly and easily for generating the desired linear pH gradient. For example, container A can have four buffer salts 32 mM MES, 20 mM MOPS, 24 mM TAPS, and 20 mM CAPSO at pH 5.6. Container B can have 20 mM MES, 24 mM MOPS, 28 mM TAPS, 32 mM CAPSO at pH 10.2. Container C can have 60 mM NaCl. Container D can have deionized water. In this embodiment, the concentration of the monovalent non-buffer ionic salt can be easily adjusted through the proportioning valve for Container C if needed. Similarly, the concentration of the buffer salts can also be easily adjusted through the proportioning valve for Containers A, B, and C if needed.

Injection valve 112 can be used to inject a bolus of a liquid sample into an eluent stream. The liquid sample may include a plurality of chemical constituents (i.e., matrix components) and one or more analytes of interest. Sample injection valve 112 will typically have two positions. In the first position, eluent will simply flow through injection valve 112 to chromatographic separation device 114. A user can load a liquid sample into a sample loop in injection valve 112 that has a predetermined volume. Once injection valve 112 is switched to the second position, eluent will flow through the sample loop and then introduce the liquid sample to chromatographic separation device 114. In an embodiment, injection valve 112 can be in the form of a six port valve.

Chromatographic separation device 114 can be used to separate various matrix components present in the liquid sample from the analyte(s) of interest. Typically, chromatographic separation device 114 may be in the form of a hollow cylinder that contains a packed stationary phase. As the liquid sample flows through chromatographic separation device 114, the matrix components and target analytes can have a range of retention times for eluting off of chromatographic separation device 114. Depending on the characteristics of the target analytes and matrix components, they can have different affinities to the stationary phase in chromatographic separation device 114. An output of chromatographic separation device 114 can be fluidically connected to detector 116 to measure the presence of the separated chemical constituents of the liquid sample. Examples of chromatographic separation devices 114, suitable for use with the buffer kits described herein, may be in the form of a cation exchange separation device, and preferably a strong cation exchange separation device. Under certain circumstances, a weak cation exchange separation device may used with the buffer kits described herein. Commercially available strong cation exchange separation devices, suitable for use with the buffer kits described herein, are MAbPac SCX-10 (Thermo Scientific Dionex, Sunnyvale, Calif., U.S.A.), Bio Mab (Agilent Technologies), Protein-Pak Hi Res CM (Waters Corp., Milford, Mass.), TSKgel CM-STAT (Tosoh Bioscience).

Detector 116 may be in the form of ultraviolet-visible spectrometer, a fluorescence spectrometer, an electrochemical detector, a conductometric detector, a charge detector, a mass spectrometer, a charged aerosol detector, an evaporative light scattering detector, a pH meter, or a combination thereof. An example of a combination detector may be an ultraviolet-visible spectrometer with a downstream pH meter that is commercially available from Thermo Scientific Dionex (PCM-3000, Sunnyvale, Calif., U.S.A.). Details regarding the charge detector that is based on a charged barrier and two electrodes can be found in US Pre-Grant Publication No. 20090218238, which is hereby fully incorporated by reference herein. The charged aerosol detector nebulizes the effluent flow and creates charged particles that can be measured as a current proportional to the analyte concentration. Details regarding the charged aerosol detector can be found in U.S. Pat. Nos. 6,544,484; and 6,568,245, which are hereby fully incorporated by reference herein. Details regarding the evaporative light scattering detector can be found in U.S. Pat. Nos. 7,847,936; and 7,911,609; 8,089,627; and International Patent Publication No. WO2010068272A1, which are hereby fully incorporated by reference herein.

An electronic circuit may include microprocessor 118, a timer, and a memory portion. Microprocessor 118 can be used to control the operation of chromatography system 100. Microprocessor 118 may be integrated into chromatography system 100 or be part of a personal computer that communicates with chromatography system 100. Microprocessor 118 may be configured to communicate with and control one or more components of chromatography system such as pump 102, injection valve 112, and detector 116. In an embodiment, microprocessor 118 can control a proportion of pumped eluent solutions and vary the proportion as a function of time.

It should be noted that with the buffer kits described herein, a feedback mechanism between the pH detector and the proportioning valve is not needed to ensure that the pH gradient is linear over the test time of the chromatogram. This is an advantage in that the linear pH gradient is simple to implement without using custom software that adjusts the proportioning value based on the measured pH values. In order to generate, a linear pH gradient, the proportion of the first eluent with respect to the second eluent is changed as a function of time. In an embodiment, this proportional change with time is linear and has only one slope, which provides for a simple to use buffer kit. It is also an advantage in that the proportional change with time is linear and does not vary according to a higher order equation such as, for example, a polynomial equation. In other situations, where a feedback mechanism between the pH detector and the proportioning valve is implemented, multiple slopes may be used at particular time intervals to provide a linear pH slope, but this causes the buffer kit system to be more complicated.

Now that the chromatography system has been described, the following will describe the method of separating at least one analyte from matrix components in a sample with a chromatographic separation device using a gradient eluent flow having a linear pH gradient. The pH gradient ranges from a first pH value to a second pH value as a function of time. In an embodiment, the first pH may be about 6 and the second pH may be about 10 where the pH changes linearly over a predetermined time period. This predetermined time period may range from about 10 to about 180 minutes, preferably range from about 10 minutes to about 60 minutes, and more preferably range from about 10 minutes to about 30 minutes. Accordingly, the slope of the linear gradient provided by the buffer kits described herein may range from about 0.04 pH units/minutes to about 0.5 pH units/minutes.

The method includes injecting the sample into injection valve 112 where the injection valve is in fluidic communication with the chromatographic separation device 114. The first eluent solution that has the first pH value is pumped into the chromatographic separation device. The first eluent solution includes a first buffer salt, a second buffer salt, a third buffer salt, and a fourth buffer salt. The second eluent solution that has the second pH value is pumped into the chromatographic separation device. The second eluent solution includes a first buffer salt, a second buffer salt, a third buffer salt, and a fourth buffer salt. For the first and second eluent solutions, the first buffer salt, the second buffer salt, the third buffer salt, and the fourth buffer salt may be MES, BES, TAPS, and CAPSO, respectively. In an embodiment that uses a column having a 10 micron particle size, the first and second eluent solution may be pumped at a flow rate ranging from about 0.5 to about 1 mL/minutes and at a pressure ranging from about 1000 to about 3000 pounds per square inch.

For the first and second eluent solutions, the first buffer salt, the second buffer salt, the third buffer salt, and the fourth buffer salt may be MES (pKa 6.1), BES (pKa 7.1), TAPS (pKa 8.4), and CAPSO (pKa 9.6), respectively. In alternative embodiments, the second buffer salt BES may be substituted with MOPS (pKa 7.2), phosphate (pKa 2.15, 7.2, 12.38), pyrophosphate (pKa 0.91, 2.10, 6.70, 9.32), or tripolyphosphate (pKa ~1, ~2, 2.8, 6.5 and 9.2), and the third buffer salt TAPS may be substituted with TRIS (pKa 8.1).

The method also includes varying a proportion of the pumped first eluent solution and the pumped second eluent solution as a function of time. The pump can also mix the two eluents together in or after the proportioning valve, but before inputting into the chromatographic separation device. For example, the proportion can be 100% of the first eluent solution and 0% of the second eluent solution for the initial 1 minute. Next, the proportion can be changed in a linear manner where the first eluent solution changes from 100% to 0% and second eluent solution changes from 0% to 100% over the next 30 minutes. The proportion of the pumped eluent solutions can be changed in a linear manner that causes a linear pH gradient to be generated. The pH value of the eluent can be measured and recorded as a function of time where this data set forms an approximately straight line from about the first pH value to the second pH value. After the linear ramp, the first eluent solution can be maintained at 0% and second eluent solution can be maintained at 100% for the next 3 minutes. As the last part of the cycle, the first eluent solution can be switched to 100% and second eluent solution can be switched to 0% for the next 6 minutes to complete the cycle.

During this method, the sample can be eluted through the chromatographic separation device. The analyte can be separated from the matrix components in the sample, and then detected at the detector.

The buffer kits described herein are configured to provide a linear pH gradient as a function of time. The straightness of the line allows for a platform method in characterizing analytes with little to no modification to the IEC process. In an embodiment, the approximately straight line has a correlation coefficient greater than 0.97, preferably greater than 0.98, and more preferably greater than 0.99, over a range where the first pH value is about 6 and the second pH value is about 10. A correlation coefficient value that is closer to unity represents the degree of straightness of the line with a perfectly straight line having a value of unity. In addition to the correlation coefficient (e.g., Pearson's correlation coefficient and denoted as $R^2$), the mean absolute percent error (MAPE) can be used to assess the straightness or linearity of the line, as shown in Equation 1.

$$MAPE = \frac{100\%}{n} \sum_{t=0}^{n} \left| \frac{pH_{meas}(t) - pH_{calc}(t)}{pH_{calc}(t)} \right| \quad \text{(Eq. 1)}$$

During the linear gradient, all of the measured pH values ($pH_{meas}$) and time values (t) can be used to generate a linear equation. Note that n represents the number of pH measurements made during linear gradient ramp. A calculated pH values $pH_{calc}(t)$ can be determined by inputting a time value t into the calculated linear equation. The difference between $pH_{meas}$ and $pH_{calc}$ represents a deviation from linearity where this difference can be converted to a percent error, an absolute value, and then calculated as a mean. A lower MAPE value that is closer to zero represents a degree of straightness that approaches a perfectly straight line. In an embodiment, the mean absolute percent error can be less than about 1.5%, preferably less than about 1.0%, and more preferably less than about 0.5%, where the first pH value is about 6 and the second pH value is about 10.

In addition to MAPE, a mean absolute error can be calculated for assessing a degree of linearity, as shown in Equation 2.

$$MAE = \frac{1}{n} \sum_{t=0}^{n} |pH_{meas} - pH_{calc}(t)| \quad \text{(Eq. 2)}$$

Similar to MAPE, a lower MAE value that is closer to zero represents a degree of straightness that approaches a perfectly straight line.

A maximum pH error (Max pH Error) can also be calculated for assessing a degree of linearity, as shown in Equation 3.

$$\text{Max pH Error} = \text{Max}|pH_{meas}(t) - pH_{calc}(t)| \quad \text{(Eq. 3)}$$

The maximum pH error can be calculated by determining the largest difference between $pH_{meas}$ and $pH_{calc}$. A lower Max pH Error value that is closer to zero represents a degree of straightness that corresponds to a perfectly straight line.

EXAMPLE 1

The following will describe the set up of chromatographic system 100 (UltiMate 3000 HPLC system, Thermo Scientific Dionex, Sunnyvale, Calif., U.S.A.) that is illustrated in FIG. 11. Pump 102 was a HPLC pump (UltiMate 3000 Biocompatible Dual-Gradient Micro Pump DGP-3600BM, Thermo Scientific Dionex, Sunnyvale, Calif., U.S.A.) that was set to a flow rate of 1 mL/minute and a pressure of 2600 PSI. Injection valve 112 (UltiMate 3000 Autosampler WPS-3000TBFC, Thermo Scientific Dionex, Sunnyvale, Calif., U.S.A.) was configured to have a 10 microliters sample loop. Chromatographic separation device 114 (MAbPac SCX-10, 10 µm, 4×250 mm from Thermo Scientific Dionex, Sunnyvale, Calif., U.S.A.) was a strong cation exchange column suitable for use in separating proteins and more particularly MAbs. The strong cation exchange resin has a particle diameter of 10 microns and the column has an inner diameter of 4 mm and a length of 250 mm. Chromatographic system 100 was configured to heat the chromatographic separation device 114 to 30° C. Detector 116 (UltiMate 3000 VWD-3400RS, Thermo Scientific Dionex, Sunnyvale, Calif., U.S.A.) was in the form of a UV-VIS spectrophotometer and set to the wavelength of 280 nanometers. After detector 116, a pH and conductivity sensor (UltiMate 3000 PCM-3000, Thermo Scientific Dionex, Sunnyvale, Calif., U.S.A.) was placed to monitor the pH of the eluent.

The first eluent solution (A) was prepared to have the following concentrations 16 mM MES, 10 mM BES, 12 mM TAPS, 10 mM CAPSO, and 30 mM NaCl at pH 5.6. The second eluent solution (B) was prepared to have the following concentrations 10 mM MES, 12 mM BES, 14 mM TAPS, 16 mM CAPSO, and 30 mM NaCl at pH 10.2.

Pump 102 was configured to provide a gradient mobile phase using a proportion of the first eluent solution (A) and second eluent solution (B). The gradient was configured to provide the following parameters shown in Table 1.

TABLE 1

| Time (minutes) | % A | % B |
| --- | --- | --- |
| 0-1 | 100 | 0 |
| 1-31 | 100-0 | 0-100 |
| 31-34 | 0 | 100 |
| 34-40 | 100 | 0 |

FIG. 1 is a graph showing pH values measured as a function of time where the first and second eluents included MES, BES, TAPS, CAPSO, and NaCl. The pH gradient was essentially linear from about pH 6 to about pH 10 over a 30 minute period. The correlation coefficient value $R^2$ was 0.9996.

Figure 2:
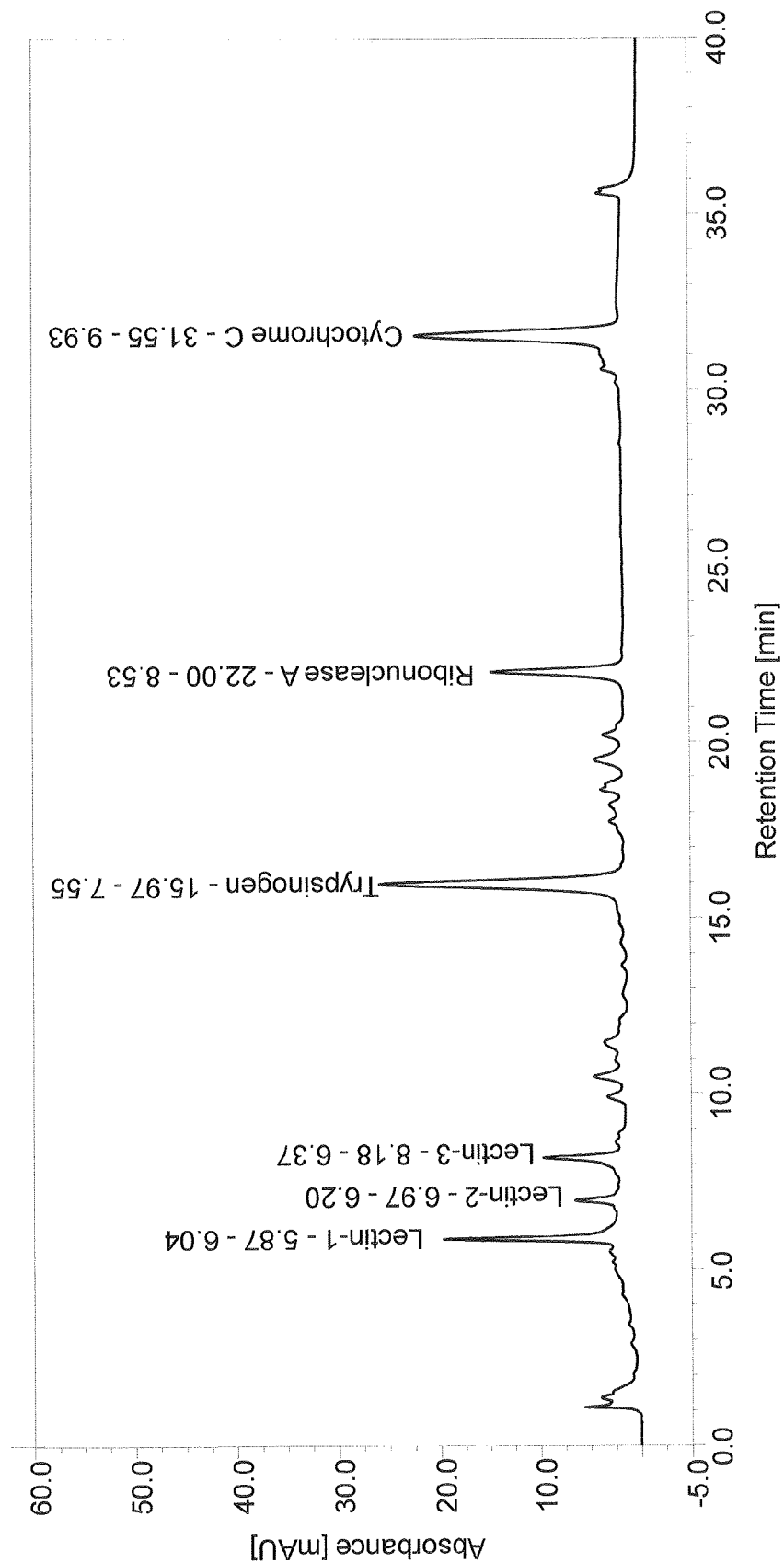
FIG. 2 is a chromatogram that uses the buffer kit of FIG. 1 and shows the retention times and corresponding pH values for peaks in a protein sample.

A protein sample, that has several constituents with a range of pI values from about 6 to about 10, was injected into chromatographic system 100. The constituents included lectins (including three isoforms, lectin-1, lectin-2, and lectin-3), trypsinogen, ribonuclease A, and cytochrome C. FIG. 2 is a chromatogram of the protein sample that used the buffer kit of this Example. For each major peak in the chromatogram, they were labeled with a constituent name, a retention time, and the pH that was measured with a slight delay time with respect to the measurement of the UV-VIS peak. The peaks had a high resolution and efficiency showing that a protein sample with a range of pI values from 6 to 10 can be effectively separated using the linear pH gradients produced with the buffer kit of this Example.

EXAMPLE 2

Figure 3:
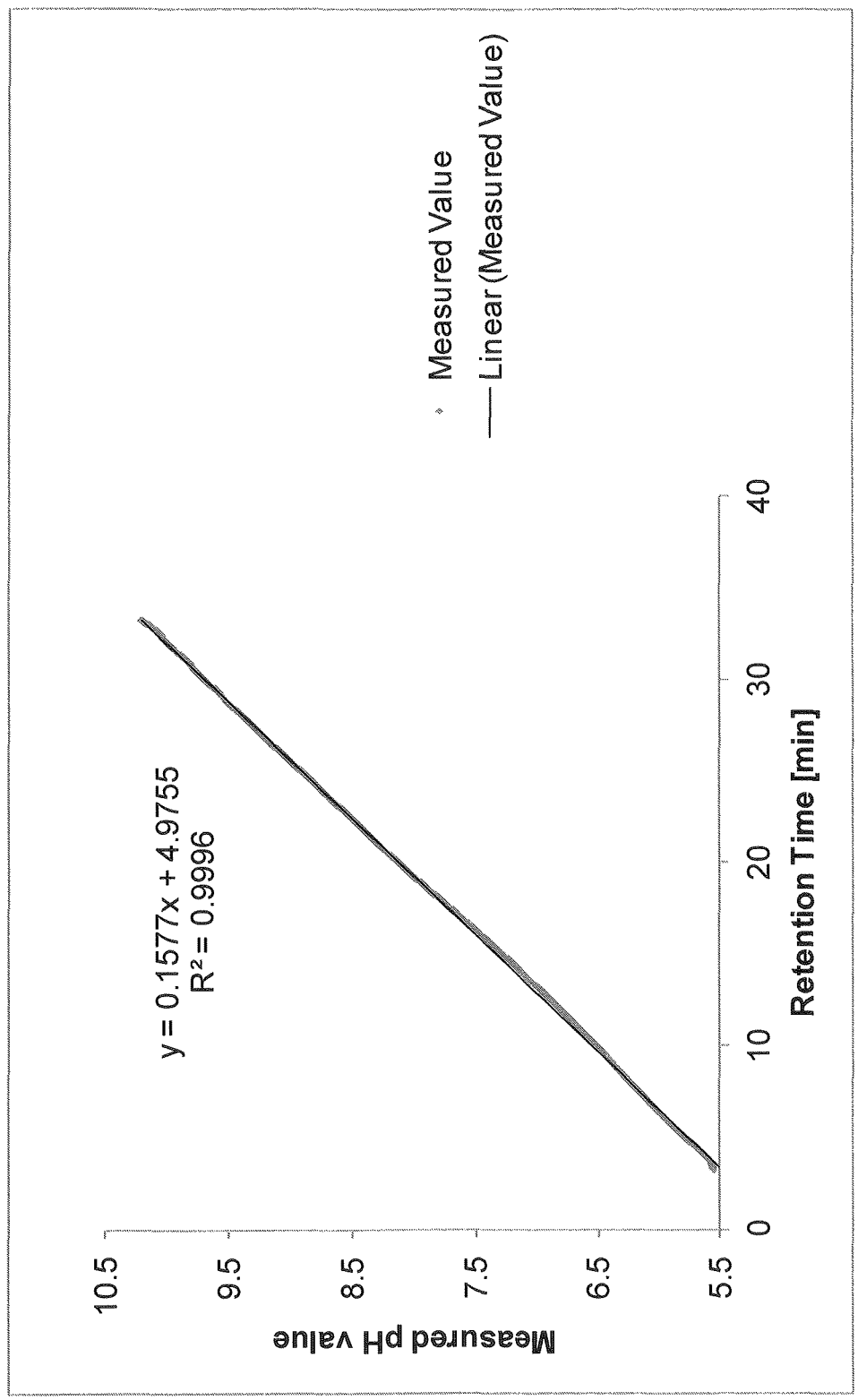
FIG. 3 is a graph showing measured pH values as a function of time using a buffer kit that includes the buffer salts of MES, MOPS, TAPS, and CAPSO.

The following will describe the use of another embodiment of a buffer kit where the second buffer salt BES from the buffer kit of Example 1 was replaced with another Good's buffer MOPS. This example used chromatographic system 100 with similar conditions as described in Example 1. The first eluent solution (A) was prepared to have the following concentrations 16 mM MES, 10 mM MOPS, 12 mM TAPS, 10 mM CAPSO, and 30 mM NaCl at pH 5.6. The second eluent solution (B) was prepared to have the following concentrations 10 mM MES, 12 mM MOPS, 14 mM TAPS, 16 mM CAPSO, and 30 mM NaCl at pH 10.2. Pump 102 was configured to provide a mobile phase gradient according to the parameters in Table 1. FIG. 3 is a graph showing pH values measured as a function of time where the first and second eluents included MES, MOPS, TAPS, CAPSO, and NaCl. The pH gradient was essentially linear from about pH 6 to about pH 10 over a 30 minute period. The correlation coefficient value $R^2$ was 0.9996, which is the same as the buffer kit of Example 1. A chromatogram was run for the protein sample of Example 1 that used the buffer kit of this Example. The resulting chromatogram was similar to one in FIG. 2 showing that a protein sample with a range of pI values from 6 to 10 can be effectively separated using the linear pH gradients produced with the buffer kit of this Example (data not shown).

EXAMPLE 3

Figure 4:
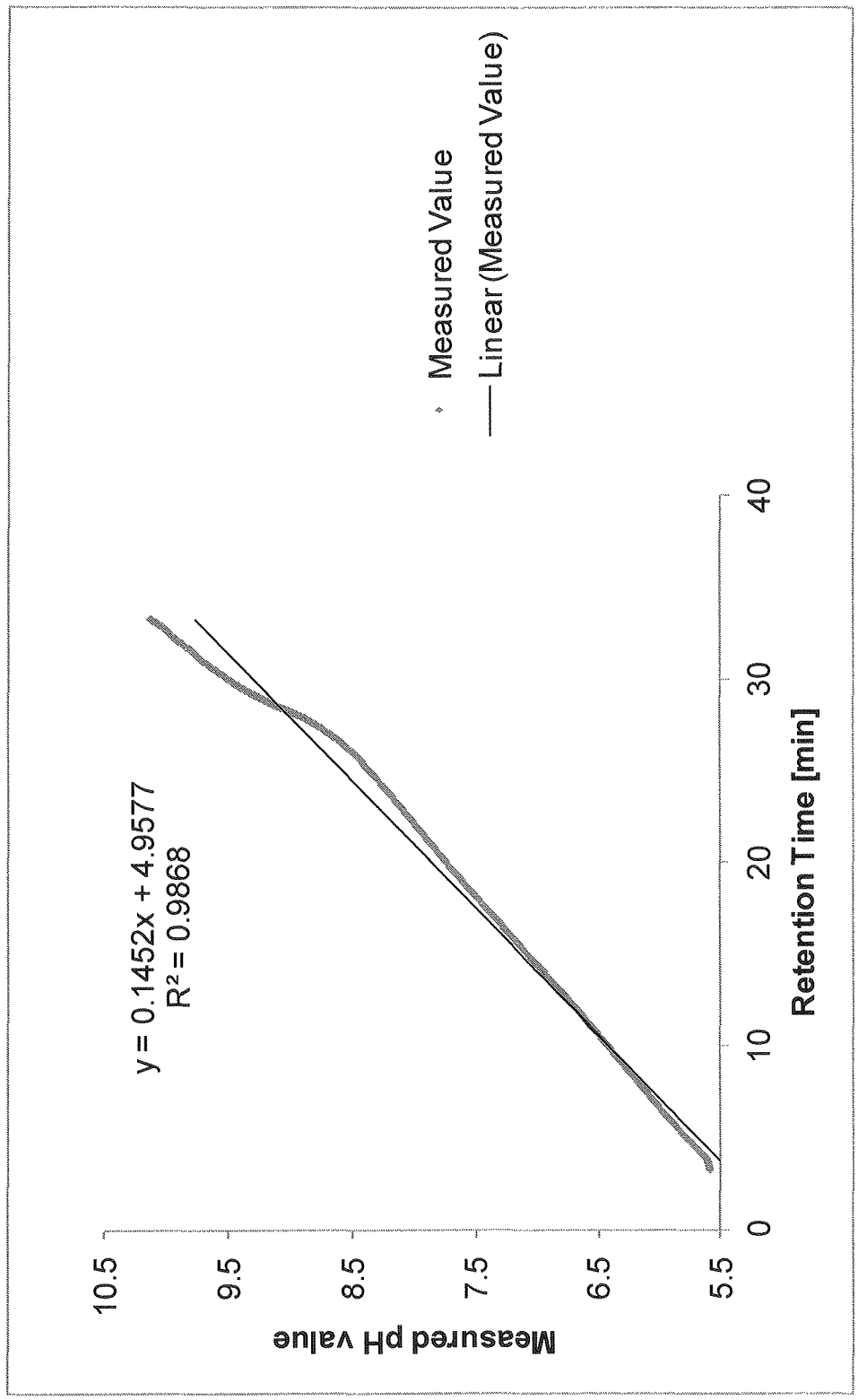
FIG. 4 is a graph showing measured pH values as a function of time using a buffer kit that includes the buffer salts of MES, BES, TRIS, and CAPSO.
Figure 6:
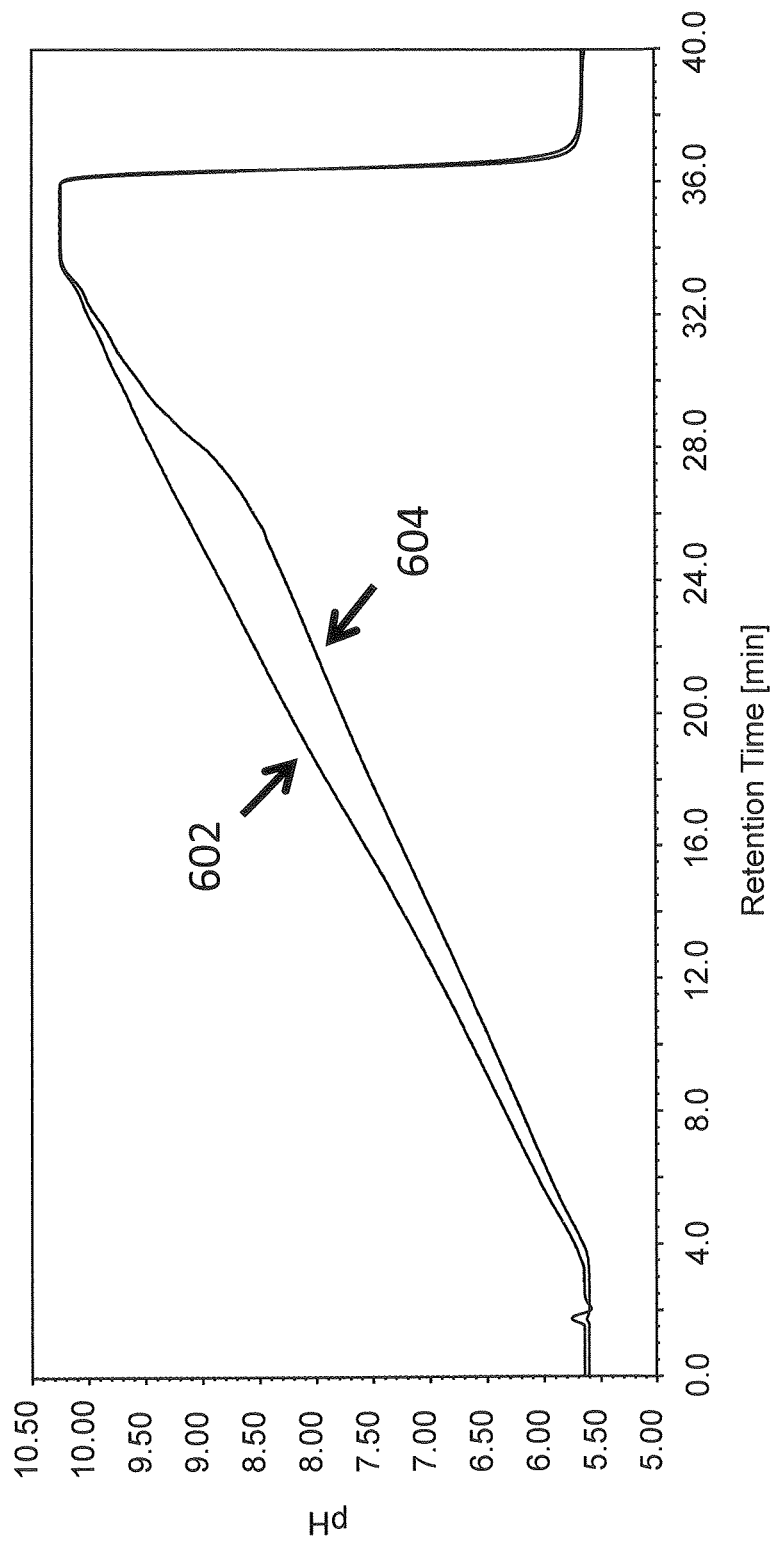
FIG. 6 is a graph comparing the linearity of pH traces when using the buffer kit that includes MES, BES, TAPS, and CAPSO of FIG. 1 (arrow 602) and the buffer kit that includes MES, BES, TRIS, and CAPSO of FIG. 4 (arrow 604).

The following will describe the use of another embodiment of a buffer kit where the third buffer salt TAPS from the buffer kit of Example 1 was replaced with another buffer TRIS. Unlike TAPS, TRIS can be either neutral or positively charged over a pH range of about 6 to about 10 and does not have a sulfonate group. This example used chromatographic system 100 with similar conditions as described in Example 1. The first eluent solution (A) was prepared to have the following concentrations 16 mM MES, 10 mM BES, 12 mM TRIS, 10 mM CAPSO, and 30 mM NaCl at pH 5.6. The second eluent solution (B) was prepared to have the following concentrations 10 mM MES, 12 mM BES, 14 mM TRIS, 16 mM CAPSO, and 30 mM NaCl at pH 10.2. Pump 102 was configured to provide a mobile phase gradient according to the parameters in Table 1. FIG. 4 is a graph showing pH values measured as a function of time where the first and second eluents included MES, BES, TRIS, CAPSO, and NaCl. The pH gradient was approximately linear from about pH 6 to about pH 10 over a 30 minute period. In this Example, the pH gradient had a more pronounced sigmoidal shape than the pH gradients of Examples 1 and 2. For comparative purposes, a graph was generated, as shown in FIG. 6, comparing the linearity of pH traces when using the buffer kit using MES, BES, TAPS, and CAPSO of Example 1 (arrow 602) and the buffer kit using MES, BES, TRIS, and CAPSO of this Example (arrow 604). The correlation coefficient value $R^2$ was 0.9868 for the buffer kit using TRIS, which is less than the buffer kit of Examples 1 and 2. A chromatogram was run for the protein sample of Example 1 that used the buffer kit of this Example. Although the buffer kit of this Example provided a slightly less linear pH gradient, the resulting chromatogram was similar to one in FIG. 2 showing that a protein sample with a range of pI values from 6 to 10 can be effectively separated using the linear pH gradients produced with the buffer kit of this Example (data not shown).

EXAMPLE 4

Figure 5:
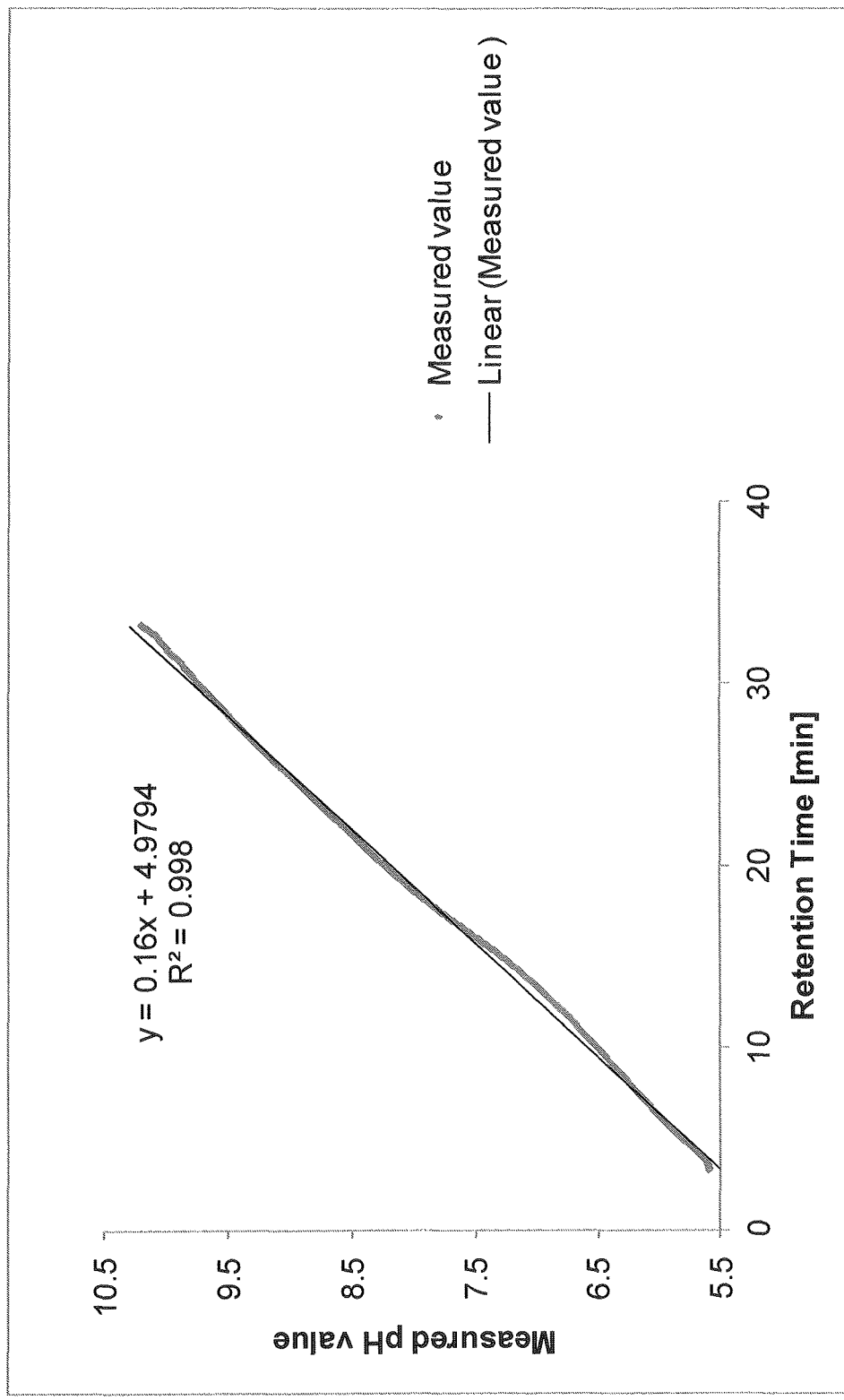
FIG. 5 is a graph showing measured pH values as a function of time using a buffer kit that includes the buffer salts of MES, phosphate, TAPS, and CAPSO.

The following will describe the use of yet another embodiment of a buffer kit where the second buffer salt BES from the buffer kit of Example 1 was replaced with another buffer salt phosphate. Unlike BES, phosphate is only negatively charged over a pH range of about 6 to about 10, is a polyvalent buffer, and does not have an amine group or a sulfonate group. This example used chromatographic system 100 with similar conditions as described in Example 1. The first eluent solution (A) was prepared to have the following concentrations 16 mM MES, 10 mM phosphate, 12 mM TAPS, 10 mM CAPSO, and 30 mM NaCl at pH 5.6. The second eluent solution (B) was prepared to have the following concentrations 10 mM MES, 12 mM phosphate, 14 mM TAPS, 16 mM CAPSO, and 30 mM NaCl at pH 10.2. Pump 102 was configured to provide a mobile phase gradient according to the parameters in Table 1. FIG. 5 is a graph showing pH values measured as a function of time where the first and second eluents included MES, phosphate, TAPS, CAPSO, and NaCl. The pH gradient was essentially linear from about pH 6 to about pH 10 over a 30 minute period. In this Example, the pH gradient had a more pronounced sigmoidal shape than the pH gradients of Examples 1 and 2, but less than Example 3. The correlation coefficient value $R^2$ was 0.998, which is about the same as the buffer kits of Examples 1 and 2. A chromatogram was run for the protein sample of Example 1 that used the buffer kit of this Example. Although the buffer kit of this Example provided a slightly less linear pH gradient, the resulting chromatogram was similar to one in FIG. 2 showing that a protein sample with a range of pI values from 6 to 10 can be effectively separated using the linear pH gradients produced with the buffer kit of this Example (data not shown).

EXAMPLE 5

Other methods of evaluating the relative straightness of the pH gradient were assessed. The correlation coefficient $R^2$ is not always the most robust process for calculating linearity, especially where the data points are on average linear. For example, a sigmoidal curve that has an approximately equal proportion of positive and negative biases will provide a correlation coefficient $R^2$ close to unity. The relative straightness of the pH gradients of Examples 1 to 4 was assessed by calculating the MAE, Max pH Error, MAPE, and $R^2$ using Equations 2 to 4, which is shown in Table 2 (note $R^2$ was calculated using Microsoft Excel).

TABLE 2

| Buffer | MAE (pH units) | Max pH Error (after 4 minutes) | MAPE (%) | $R^2$ |
| --- | --- | --- | --- | --- |
| MES, BES, TAPS, CAPSO-Example 1 | 0.023 | 0.062 | 0.29 | 0.9996 |
| MES, MOPS, TAPS, CAPSO-Example 2 | 0.022 | 0.048 | 0.30 | 0.9996 |
| MES, BES, TRIS, CAPSO-Example 3 | 0.118 | 0.368 | 1.43 | 0.9868 |
| MES, Phosphate, TAPS, CAPSO-Example 4 | 0.055 | 0.103 | 0.72 | 0.998 |

The buffer kits of Examples 1 and 2 showed the lowest MAPE value, and thus, were the most linear. Example 3 showed a MAPE value almost 5-fold larger than Examples 1 and 2. Example 4 showed a MAPE value about 2-fold larger than Examples 1 and 2. It should also be noted that the trends of the MAE and Max pH Error approximately tracked with the MAPE values.

EXAMPLE 6

An analysis was performed to show that there is a correlation between the elution pH for the peaks and the corresponding pI values of the protein components. Referring back to FIG. 2, the pH values for six of the chromatographic peaks were recorded that corresponded to the approximate pH value of the effluent at the time that the peak was detected by the UV detector. The six chromatographic peaks, listed in sequential order, were for lectin-1, lectin-2, lectin-3, trypsinogen, ribonuclease A, and cytochrome C, which have literature based pI values of about 7.8, 8.0, 8.2, 8.7, 9.3, and 10.2, respectively.

Figure 7:
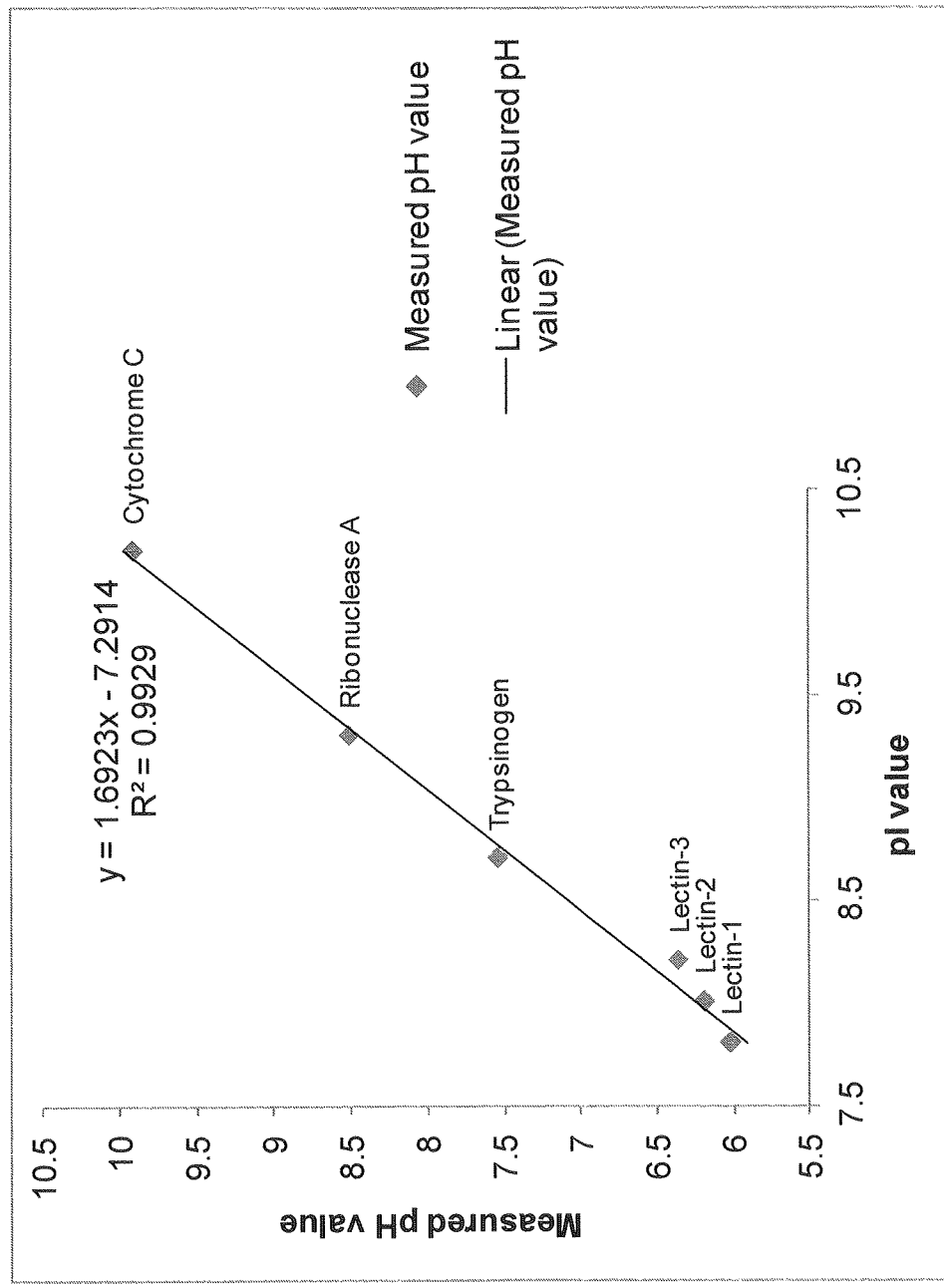
FIG. 7 is a graph comparing the measured pH values for six protein component peaks as a function of the corresponding pI values when using the buffer kit that includes MES, BES, TAPS, and CAPSO of FIG. 1.

FIG. 7 is a graph comparing the measured pH values for six protein component peaks as a function of the corresponding pI values when using the buffer kit that includes MES, BES, TAPS, and CAPSO of FIG. 1. The measured pH values for the six protein component peaks exhibited a strong linear correlation to the literature based pI values. Thus, after a calibration procedure, this Example supports the fact that linear regression coupled with the buffer kits described herein can be used to estimate the pI of a protein component based on the peak retention time and measured pH. It should be noted that similar experiments for the buffer kits of Examples 2 to 4 were performed and also showed that the retention times can be used to estimate the pI of the protein components (data not shown).

EXAMPLE 7

Figure 8:
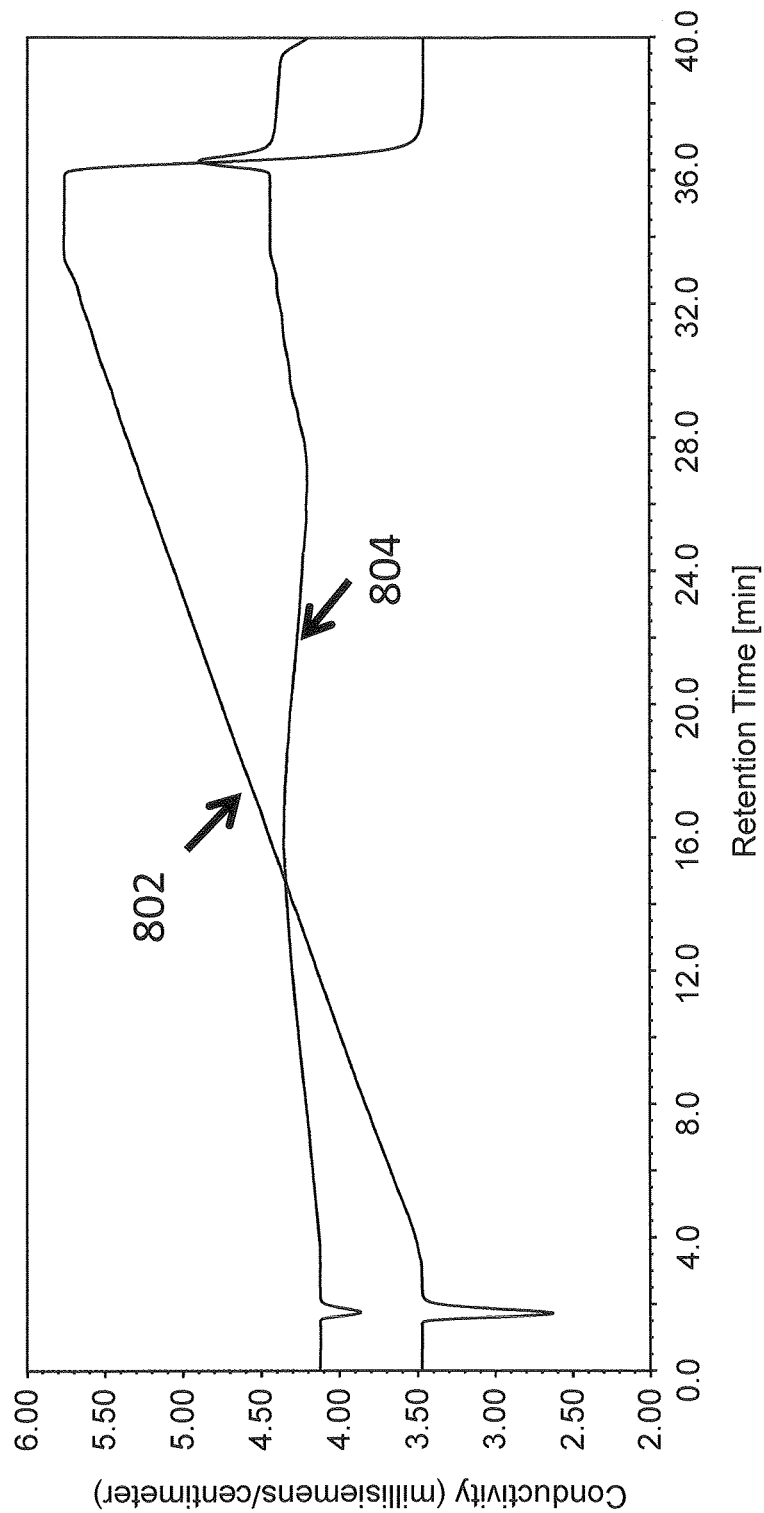
FIG. 8 is a graph showing conductivity values as a function of time using the buffer kit that includes MES, BES, TAPS, and CAPSO of FIG. 1 (arrow 802) and the buffer kit that includes MES, BES, TRIS, and CAPSO of FIG. 4 (arrow 804).

The conductivity profile as a function of time was studied for the buffer kits of Example 1 and 3. This example used chromatographic system 100 with similar conditions as described in Example 1. In this Example, the data from the conductivity detector was also analyzed. The conductivity detector was in fluidic contact with an output of the chromatographic separation device. Pump 102 was configured to provide a mobile phase gradient according to the parameters in Table 1. FIG. 8 is a graph showing conductivity values as a function of time using the buffer kit with MES, BES, TAPS, and CAPSO of Example 1 (arrow 802) and the buffer kit with MES, BES, TRIS, and CAPSO of Example 3 (arrow 804). For the buffer kit of Example 1, it showed an approximately linear increase in measured conductivity values. In contrast, for the buffer kit of Example 3, it showed an approximately linear line that was essentially flat with approximately constant measured conductivity values. Thus, the replacement of the Good's buffer TAPS with TRIS caused the conductivity profile to no longer be linearly increasing. Applicant believes that in addition to a linearly increasing pH gradient, a linearly increasing salt concentration gradient helps focus and sharpen the chromatographic peak shapes. Applicant believes that an approximately flat salt concentration profile can allow acceptable chromatograms, but at slightly less than optimal performance. However, Applicant believes that a decreasing salt concentration profile will degrade performance by defocusing the chromatographic peak shapes.

EXAMPLE 8

Figure 9:
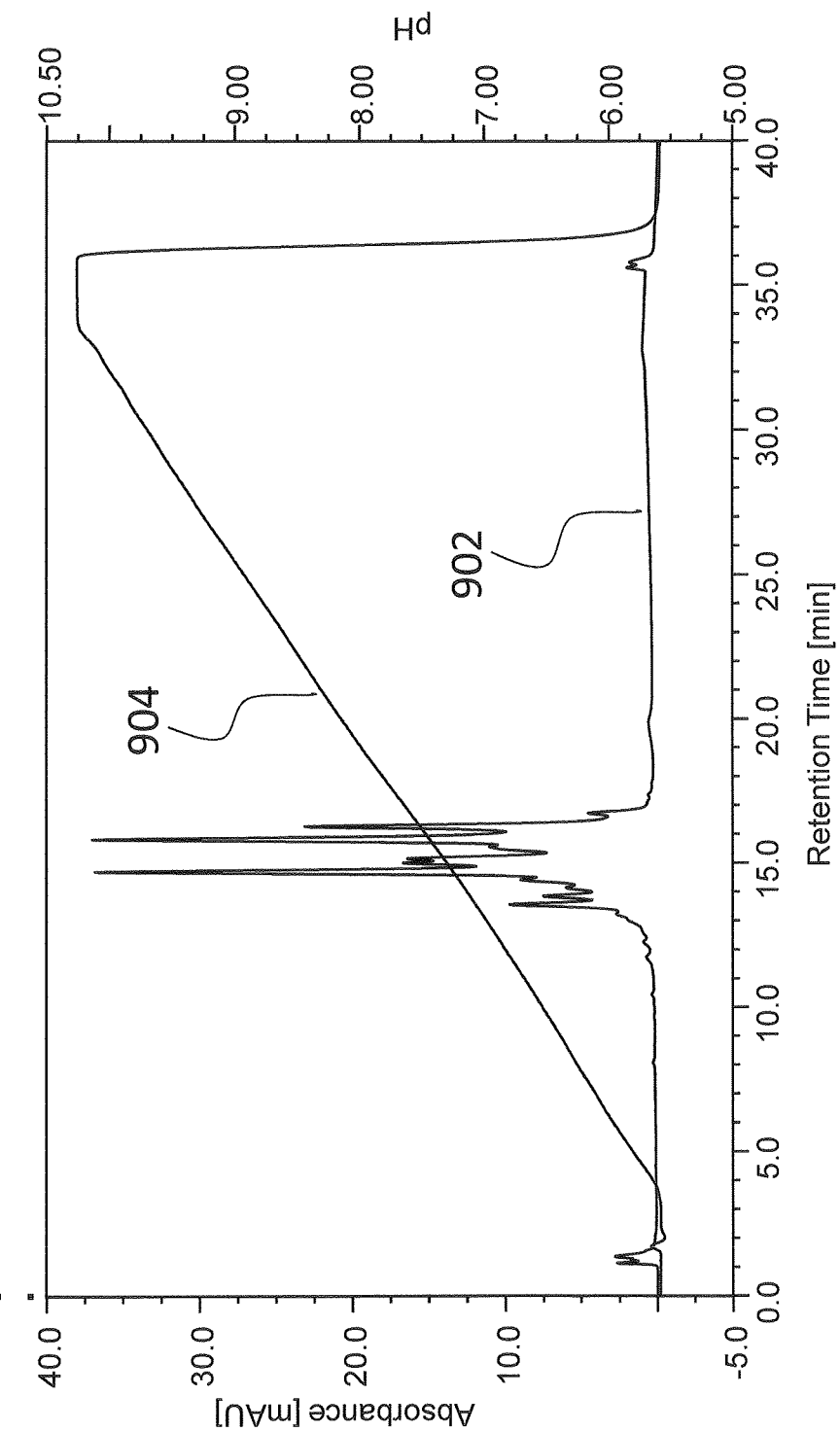
FIG. 9 is an exemplary chromatogram (902) that characterizes the various charge variants of a heterogeneous MAb sample using a linear pH gradient ranging from about pH 5.6 to 10.2 over a 30 minute period. The trace 904 shows the measured pH as a function of time.

The following will describe the separation of a heterogeneous MAb sample that includes various charge variants using the buffer kit of Example 2. This example used chromatographic system 100 with similar conditions as described in Example 2. Pump 102 was configured to provide a mobile phase gradient according to the parameters in Table 1. FIG. 9 is a chromatogram that illustrates various peaks that correspond to the charged variants where the chromatographic trace is denoted by leading line 902. In addition, FIG. 9 shows the linear pH profile as a function of time that is denoted by leading line 904. In summary, the buffer kit of Example 2 provided a linear pH gradient sufficient to provide an excellent separation and characterization of a heterogeneous MAb sample.

EXAMPLE 9

The following will illustrate one of the advantages of a linear pH gradient having a high degree of straightness, which allows high resolution chromatograms to be generated. Referring back to FIG. 9, the largest cluster of peaks eluted off of the chromatographic separation device is at about pH 6.7 to 7.9, with a relatively small number of peaks at less than pH 6.7 and greater than 7.9. A subsequent higher resolution chromatogram with a narrower pH range can be implemented using the buffer kit of Example 1. The resolution of the chromatogram can be increased by simply reducing the rate of pH change per unit time as shown in Table 3.

TABLE 3

| Time (minutes) | % A | % B |
|---|---|---|
| 0-1 | 75 | 25 |
| 1-31 | 75-50 | 25-50 |
| 31-34 | 50 | 50 |
| 34-40 | 75 | 25 |

Figure 10:
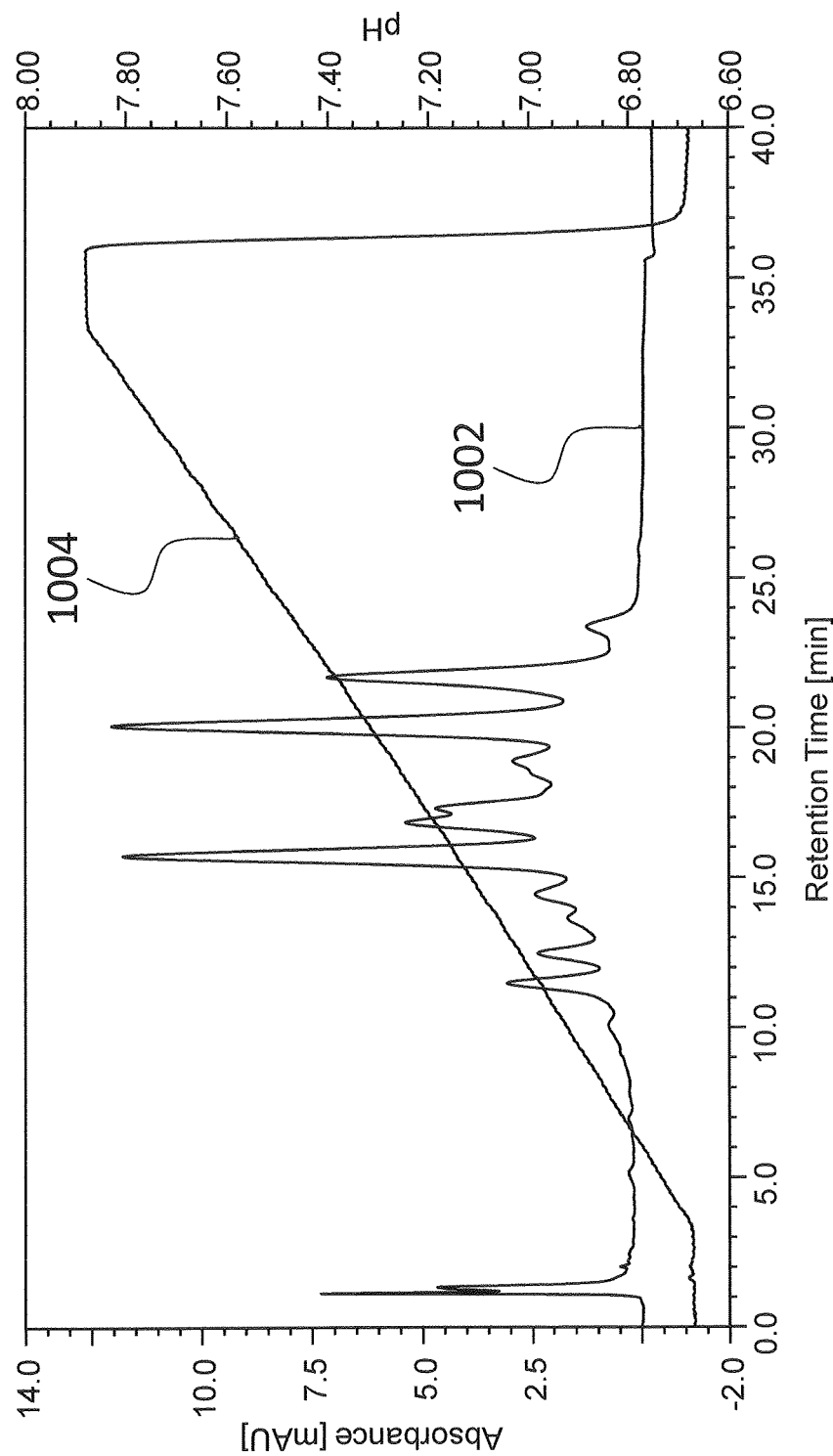
FIG. 10 is an exemplary chromatogram (1002) that characterizes the various charge variants of the heterogeneous MAb sample of FIG. 9 using a linear pH gradient ranging from about pH 6.7 to 7.9 over a 30 minute period, where the rate of pH change per unit time is less than that of FIG. 9. The trace 1004 shows the measured pH as a function of time.

Instead of changing the pH by 4 units over a 30 minute time interval, the pH units were changed by about 1.2 units over the same time interval. Because the buffer kit of Example 1 has a high degree of linearity, the lower pH rate change as a function of time will also have a high degree of linearity allowing the buffer kit to be a platform method that is proportional and scalable. FIG. 10 is a chromatogram that illustrates various peaks that correspond to a portion of the charged variants in FIG. 9, but with higher resolution (i.e., increased spacing in between peaks). The chromatographic trace is denoted by a leading line 1002 and the linear pH trace is denoted by a leading line 1004. Thus, not only did the buffer kit of Example 2 provide a linear pH gradient sufficient to provide excellent separation of a heterogeneous MAb sample, but it was able to provide a higher resolution separation by merely decreasing the rate of pH change as a function of time.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A buffer kit comprising:
   a) a first eluent solution including at least four buffer salts where at least three of the four buffer salts are a monovalent buffer salt, have a net negative charge or a net neutral zwitterionic charge over a pH range of about 6 to about 10, and include a sulfonate group and an amine, where the first eluent solution has a first pH of about 6 and a total buffer salt concentration of greater than about 25 millimolar;

b) a second eluent solution including at least four buffer salts where at least three of the four buffer salts are a monovalent buffer salt, have a net negative charge or a net neutral zwitterionic charge over a pH range of about 6 to about 10, and include a sulfonate group and an amine, where the second eluent solution has a second pH of about 10 and a total buffer salt concentration of greater than about 25 millimolar;

whereby the buffer kit provides a linear pH gradient, based on a function of time and pH values, that forms an approximately straight line for at least a pH range of about pH 6 to about pH 10.

2. The buffer kit of claim 1, in which the first eluent solution and the second eluent solution each further include a monovalent non-buffer ionic salt selected from the group consisting of sodium chloride, potassium chloride, sodium methanesulfonate, and a combination thereof.

3. The buffer kit of claim 2, in which the monovalent non-buffer ionic salt has a concentration of about 15 millimolar or greater.

4. The buffer kit of claim 1, in which for the first eluent solution, a highest buffer concentration of the at least four buffer salts is not greater by more than about 60% of a lowest buffer concentration of the at least four buffer salts.

5. The buffer kit of claim 1, in which for the second eluent solution, a highest buffer concentration of the at least four buffer salts is not greater by more than about 60% of a lowest buffer concentration of the at least four buffer salts.

6. The buffer kit of claim 1, in which the four buffer salts of the first eluent solution comprise:
a first buffer salt that includes 2-(N- morpholino)ethanesulfonate (MES),
a second buffer salt that includes 3-(N-morpholino)propanesulfonate (MOPS),
a third buffer salt that includes (tris(hydroxymethyl)methylamino)propane-1-sulfonate (TAPS), and
a fourth buffer salt that includes 3-(cyclohexylamino)2-hydroxy-1-propanesulfonate (CAPSO).

7. The buffer kit of claim 1, in which the four buffer salts of the first eluent solution comprise:
a first buffer salt that includes 2-(N-morpholino)ethanesulfonate (MES),
a second buffer salt that includes N,N-bis(2-hydroxyethyl)-2-aminoethanesulfonate (BES),
a third buffer salt that includes (tris(hydroxymethyl)methylamino)propane-1-sulfonate (TAPS), and
a fourth buffer salt that includes 3-(cyclohexylamino)-2-hydroxy-1-propanesulfonate(CAPSO).

8. The buffer kit of claim 1, in which the four buffer salts of the second eluent solution comprise:
a first buffer salt that includes 2-(N-morpholino)ethanesulfonate (MES),
a second buffer salt that includes 3-(N-morpholino)propanesulfonate (MOPS),
a third buffer salt that includes (tris(hydroxymethyl)methylamino)propane-1-sulfonate (TAPS), and
a fourth buffer salt that includes 3-(cyclohexylamino)-2-hydroxy-1-propanesulfonate(CAPSO).

9. The buffer kit of claim 1, in which the four buffer salts of the second eluent solution comprise:
a first buffer salt that includes 2-(N-morpholino)ethanesulfonate (MES),
a second buffer salt that includes N,N-bis(2-hydroxyethyl)-2-aminoethanesulfonate (BES),
a third buffer salt that includes (tris(hydroxymethyl)methylamino)propane-1-sulfonate (TAPS), and
a fourth buffer salt that includes 3-(cyclohexylamino)-2-hydroxy-1-propanesulfonate (CAPSO).

10. The buffer kit of claim 1, in which the at least four buffer salts, for both the first eluent solution and the second eluent solution, each have a net negative charge or a net neutral charge over a pH range of about 6 to about 10.

11. The buffer kit of claim 1, in which one of the at least four buffer salts, for both the first eluent solution and the second eluent solution, is selected from the group consisting of tris(hydroxymethyl)aminomethane (TRIS) and phosphate.

12. The buffer kit of claim 1, in which the at least four buffer salts of the first eluent solution and second eluent solution, each comprise a first buffer salt that has a first pKa, a second buffer salt that has a second pKa, a third buffer salt that has a third pKa, and a fourth buffer salt that has a fourth pKa, where the first pKa is the smallest of the four pKa values and the fourth pKa is the largest of the four pKa values, and that the first pKa is about the same as the first pH value and that the fourth pKa is about the same as the second pH value, in which the at least four buffer salts have a first difference between the second pKa and the first pKa that is less than about 1.5, a second difference between the third pKa and the second pKa that is less than about 1.5, and a third difference between the third pKa and the fourth pKa that is less than about 1.5.

13. The buffer kit of claim 1, in which the straight line for the pH range of about pH 6 to about pH 10 has a correlation coefficient greater than about 0.97.

14. The buffer kit of claim 1, in which the straight line for the pH range of about pH 6 to about pH 10 has a mean absolute percent error of less than about 1.4%.

15. The buffer kit of claim 1, in which the amine is in a protonated ammonium form.

16. A method of separating at least one analyte from matrix components in a sample with a chromatographic separation device using a gradient eluent flow having a linear pH gradient from a first pH value to a second pH value as a function of time, the method comprising:
injecting the sample into an injection valve, the injection valve being in fluidic communication with the chromatographic separation device;
pumping a first eluent solution that has the first pH value into the chromatographic separation device, the first eluent solution comprising: a first buffer salt, a second buffer salt, a third buffer salt, and a fourth buffer salt, where at least three of the four buffer salts for the first eluent solution are a monovalent buffer salt, have a net negative charge or a net neutral zwitterionic charge over a pH range of about 6 to about 10, and include a sulfonate group and an amine;
pumping a second eluent solution that has the second pH value into the chromatographic separation device, the second eluent solution comprising: a first buffer salt, a second buffer salt, a third buffer salt, and a fourth buffer salt, where at least three of the four buffer salts for the second eluent solution are a monovalent buffer salt, have a net negative charge or a net neutral zwitterionic charge over a pH range of about 6 to about 10, and include a sulfonate group and an amine,
for both the first and second eluent solutions, the first buffer salt has a first pKa, the second buffer salt has a second pKa, the third buffer salt has a third pKa, and the fourth buffer salt has a fourth pKa, where the first pKa is the smallest of the four pKa values and the fourth pKa is the largest of the four pKa values, and that the first pKa is about the same as the first pH value and that the fourth pKa is about the same as the second pH value, a first difference between the second pKa and the first pKa is less than about 1.5, a second difference between the third pKa and the second pKa is less than about 1.5, and a third difference between the third pKa and the fourth pKa is less than about 1.5;

varying a proportion of the pumped first eluent solution and the pumped second eluent solution as a function of time;

generating a linear pH gradient based on a function of time and pH values, that forms an approximately straight line from about the first pH value to the second pH value;

eluting the sample through the chromatographic separation device;

separating the analyte from matrix components in the sample; and detecting the analyte at a detector.

17. The method of claim 16, in which the linear pH gradient is an approximately straight line with a correlation coefficient greater than 0.97, where the first pH value is about 6 and the second pH value is about 10.

18. The method of claim 16, in which the linear pH gradient is an approximately straight line with a mean absolute percent error of less than about 1.4%, where the first pH value is about 6 and the second pH value is about 10.

19. The method of claim 16 further comprising:
generating a linear conductivity gradient, at the same time, as the step of generating the linear pH gradient in which the generated linear pH gradient has increasing pH values as a function of time and the generated linear conductivity gradient has increasing conductivity values as a function of time.

20. The method of claim 16, in which the chromatographic separation device comprises a cation exchange resin where each of the buffer salts for the first and second eluent solutions do not bind to the cation exchange resin.

21. The method of claim 16, in which the analyte comprises an antibody.

22. The method of claim 16, in which the generated linear pH gradient is formed in the chromatographic separation device.

23. The method of claim 16, in which for both the first eluent solution and the second eluent solution, the first buffer salt comprises 2-(N-morpholino)ethanesulfonate (MES).

24. The method of claim 16, in which for both the first eluent solution and the second eluent solution, the second buffer salt is selected from the group consisting of 2-[bis(2-hydroxyethyl)amino]ethanesulfonate (BES), 3-(N-morpholino)propanesulfonate (MOPS), and phosphate.

25. The method of claim 16, in which for both the first eluent solution and the second eluent solution, the third buffer salt is selected from the group consisting of N-[tris(hydroxymethyl)methyl]-3-aminopropanesulfonate (TAPS), N-(2-piperazine-hydroxyethyl) N'-(4-butanesulfonate) (HEPBS), and tris(hydroxymethyl)aminomethane (TRIS).

26. The method of claim 16, in which for both the first eluent solution and the second eluent solution, the fourth buffer salt is selected from the group consisting of 3-(cyclohexylamino)-2-hydroxy1-propanesulfonate (CAPSO) and 2-(cyclohexylamino) ethanesulfonate (CHES).

27. The method of claim 16, in which the first eluent solution and second eluent solution each further comprise a monovalent non-buffer ionic salt selected from the group consisting of sodium chloride, potassium chloride, sodium methanesulfonate, and a combination thereof.

28. The method of claim 27, in which the monovalent non-buffer ionic salt has a concentration of about 15 millimolar or greater.

29. The method of claim 16, in which the first pH value is about 6 and the second pH value is about 10.

30. The method of claim 16, in which the first and second eluent solutions each have a total buffer salt concentration of greater than about 25 millimolar.

31. The method of claim 16, in which for the first eluent solution, a highest buffer concentration of the four buffer salts is not greater by more than about 60% of a lowest buffer concentration of the four buffer salts.

32. The method of claim 16, in which for the second eluent solution, a highest buffer concentration of the four buffer salts is not greater by more than about 60% of a lowest buffer concentration of the four buffer salts.

33. The method of claim 16 further comprising:
before the pumping of the first eluent solution and the second eluent solution into the chromatographic separation device, mixing the first eluent solution and the second eluent solution together.

34. The method of claim 16 further comprising:
inputting two or more solutions sources into a pump, where a combination of the two or more solutions sources together includes: the first buffer salt, the second buffer salt, the third buffer salt, and the fourth buffer salt of the first eluent solution;
forming the first eluent solution from the two or more solution sources.

35. The method of claim 16 further comprising:
inputting two or more solutions sources into a pump, where a combination of the two or more solutions sources together includes: the first buffer salt, the second buffer salt, the third buffer salt, and the fourth buffer salt of the second eluent solution;
forming the second eluent solution from the two or more solution sources.

36. The method of claim 16, in which each of the buffer salts are a monovalent buffer salt, have a net negative charge or a net neutral zwitterionic charge over a pH range ranging from about the first pH value to about the second pH value, and include a sulfonate group and an amine.

37. The method of claim 36, in which the amine is in a protonated ammonium form.

38. A buffer kit comprising:
a) a first eluent solution consisting of a first buffer salt, a second buffer salt, a third buffer salt, a fourth buffer salt, and a monovalent non-buffer ionic salt, where the first eluent solution has a first pH of about 6 and a total buffer salt concentration of greater than about 25 millimolar; and
b) a second eluent solution consisting of a first buffer salt, a second buffer salt, a third buffer salt, a fourth buffer salt, and a monovalent non-buffer ionic salt, where the second eluent solution has a second pH of about 10 and a total buffer salt concentration of greater than about 25 millimolar;
in which each of the buffer salts are a monovalent buffer salt, have a net negative charge or a net neutral zwitterionic charge, and include a sulfonate group and an amine.

39. The buffer kit of claim 38, in which the four buffer salts of the first eluent solution and second eluent solution, each comprise a first buffer salt that has a first pKa, a second buffer salt that has a second pKa, a third buffer salt that has a third pKa, and a fourth buffer salt that has a fourth pKa, where the first pKa is the smallest of the four pKa values and the fourth pKa is the largest of the four pKa values, and that the first pKa is about the same as the first pH value and that the fourth pKa is about the same as the second pH value, in which the at least four buffer salts have a first difference between the second pKa and the first pKa that is less than about 1.5, a second difference between the third pKa and the second pKa that is less than about 1.5, and a third difference between the third pKa and the fourth pKa that is less than about 1.5.

40. The buffer kit of claim 38, in which for the first eluent solution, a highest buffer concentration of the four buffer salts is not greater by more than about 60% of a lowest buffer concentration of the four buffer salts.

41. The buffer kit of claim 38, in which for the second eluent solution, a highest buffer concentration of the four buffer salts is not greater by more than about 60% of a lowest buffer concentration of the four buffer salts.

* * * * *